United States Patent
Smith, III

(10) Patent No.: US 6,878,830 B2
(45) Date of Patent: Apr. 12, 2005

(54) CATALYTIC BORONATE ESTER SYNTHESIS FROM BORON REAGENTS AND HYDROCARBONS

(75) Inventor: Milton R. Smith, III, East Lansing, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 24 days.

(21) Appl. No.: 10/194,809

(22) Filed: Jul. 12, 2002

(65) Prior Publication Data
US 2003/0109380 A1 Jun. 12, 2003

Related U.S. Application Data
(60) Provisional application No. 60/305,107, filed on Jul. 13, 2001.

(51) Int. Cl.$^7$ ............................................. C07D 207/00
(52) U.S. Cl. ....................... 548/402; 548/405; 548/413; 502/154
(58) Field of Search .......................... 502/154; 548/402, 548/405, 413

(56) References Cited

U.S. PATENT DOCUMENTS 5,574,171 A * 11/1996 Ayers et al. ................. 549/206
6,451,937 B1 * 9/2002 Hartwig et al. ............. 526/126

* cited by examiner

Primary Examiner—Kamal Saeed
(74) Attorney, Agent, or Firm—Ian C. McLeod

(57) ABSTRACT

A process for producing a ring-substituted arene borane which comprises reacting a ring-substituted arene with an HB organic compound in the presence of a catalytically effective amount of an iridium or rhodium complex with three or more substituents, excluding hydrogen, bonded to the iridium or rhodium and a phosphorus organic ligand, which is at least in part bonded to the iridium or rhodium, to form the ring-substituted arene borane. Also provided are catalytic compounds for catalyzing the process comprising an iridium or rhodium complex with three or substituents, excluding hydrogen, bonded to the iridium or rhodium and optionally, a phosphorus organic ligand, which is at least in part bonded to the iridium or rhodium.

23 Claims, 2 Drawing Sheets

16　　　　　　　　17　　　　　　　　18

19　　　　　　　　21　　　　　　　　20

22　　　　　　　　23　　　　　　　　24

25　　　　　　　　26　　　　　　　　27

CATALYTIC BORONATE ESTER SYNTHESIS FROM BORON REAGENTS AND HYDROCARBONS

CROSS-REFERENCE TO RELATED APPLICATION

Figure 1:
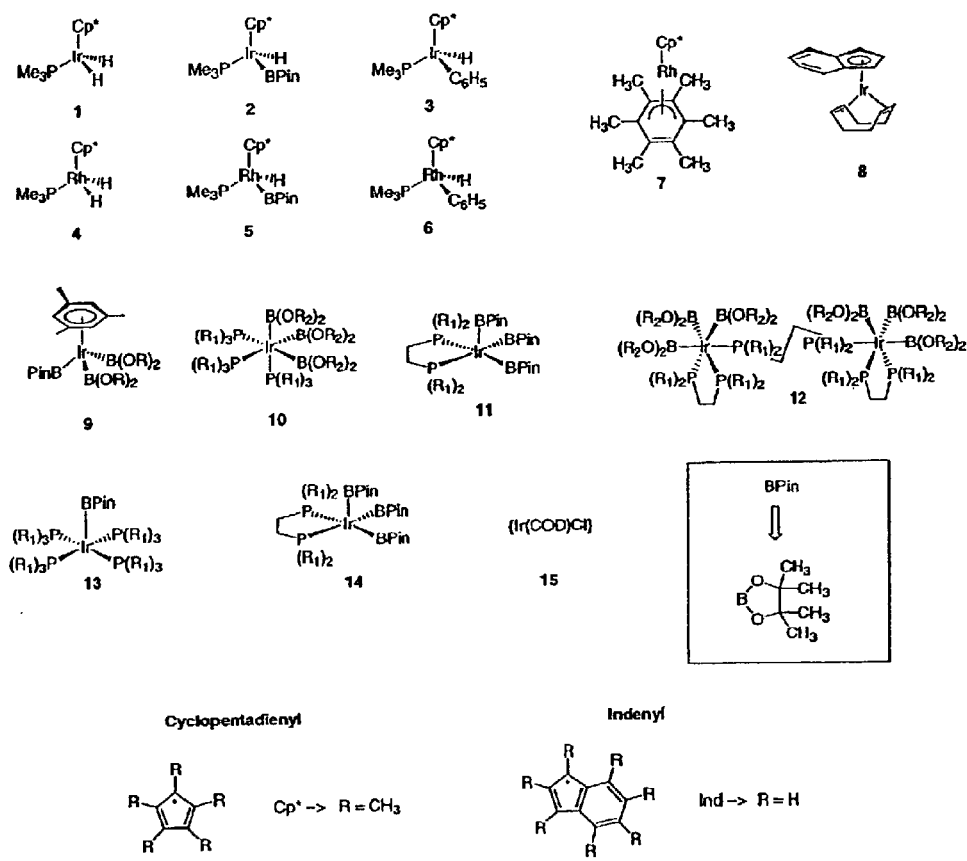

This application claims priority to Provisional Application No. 60/305,107, filed Jul. 13, 2001.

STATEMENT REGARDING FEDERALLY SPONSORED RESEARCH OR DEVELOPMENT

This invention was supported in part by National Institutes of Health, National Institute of General Medical Sciences Grant No. R01 GM63188-01 and in part by National Science Foundation Grant No. CHE-9817230. The U.S. government has certain rights in this invention.

REFERENCE TO A "COMPUTER LISTING APPENDIX SUBMITTED ON A COMPACT DISC"

Not Applicable.

BACKGROUND OF THE INVENTION

(1) Field of the Invention

The present invention relates to a process for producing a ring-substituted arene borane which comprises reacting a ring-substituted arene with an HB organic compound in the presence of a catalytically effective amount of an iridium or rhodium complex with three or more substituents, excluding hydrogen, bonded to the iridium or rhodium and a phosphorus organic ligand, which is at least in part bonded to the iridium or rhodium, to form the ring-substituted arene borane. The present invention further relates to compounds for catalyzing the process comprising an iridium or rhodium complex with three or substituents, excluding hydrogen, bonded to the iridium or rhodium and optionally, a phosphorus organic ligand, which is at least in part bonded to the iridium or rhodium.

(2) Description of Related Art

Alkyl and arylboronic esters and acids are versatile alkyl and aryl transfer reagents in organic chemistry wherein the boron serves as a "mask" for a broad range of heteroatoms and functional groups. Some of the most remarkable and broadly used applications of organoboron chemistry are catalytic cross-coupling reactions of C—B and C—X (X=Cl, Br, or I) groups which yield new C—C bonds as shown below.

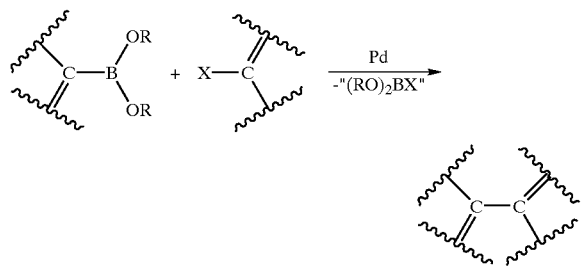

In the pharmaceutical industry, organoboron complexes are key building blocks for drug manufacturing, versatile reagents for high-throughput parallel synthesis in drug discovery, and exhibit some useful and unique biological activities.

Arylboronate esters and the corresponding acids are presently prepared by reacting Grignard reagents generated from halogenated aromatics and magnesium metal with alkyl borate reagents. A related method involves the reaction of alkyllithium reagents with aromatic halides or arenas to generate lithium reagents which are subsequently reacted with alkyl borates. Significant limitations of the current technologies include: (1) the reactions are run in ethereal solvents, (2) halogenated aromatics must be synthesized from hydrocarbon feedstocks, (3) for large-scale synthesis, unreacted chlorinated aromatic starting materials and biaryl byproducts can create significant environmental hazards and pose waste disposal problems, (4) in some instances attempted product isolation has resulted in explosions attributed to unreacted lithium and magnesium intermediates, (5) Grignard and organolithium reagents can be incompatible with a range of common functional groups including esters, amides, bromides, chlorides, iodides, alcohols, acids, and the like, and (6) cryogenic cooling is sometimes required to prevent side reactions.

In light of the above limitations of the current processes for producing boronate esters and acids, there remains a need for a general synthetic route to synthesizing boronate esters and acids which does not have the limitations of the current processes.

SUMMARY OF THE INVENTION

The present invention provides a catalytic composition comprising an iridium or rhodium complex with three or more substituents, excluding hydrogen, bonded to the iridium or rhodium. In a further embodiment, the present invention provides a catalytic composition comprising an iridium or rhodium complex with three or more substituents, excluding hydrogen, bonded to the iridium or rhodium and a ligand selected from the group consisting of a phosphorus organic ligand, an organic amine, an imine, a nitrogen heterocycle, and an ether in a molar ratio between about 1 to 3 and 1 to 1, wherein the ligand is at least in part bonded to the iridium or rhodium.

In a preferred embodiment of the present invention, the phosphorus organic ligand is selected from the group consisting of trimethyl phosphine (PMe$_3$), 1,2-bis(dimethylphosphino)ethane (dmpe), and 1,2-bis(diphenylphosphino)ethane (dppe).

In a further embodiment of the catalytic composition, the iridium complex is (ArH)Ir(BY)$_3$ wherein ArH is selected from the group consisting of aromatic, heteroaromatic, polyaromatic, and heteropolyaromatic hydrocarbon; and BY is a boron moiety.

In a further embodiment of the catalytic composition, the iridium complex is (MesH)Ir(BY)$_3$ wherein MesH is mesitylene; and BY is a boron moiety.

In a further embodiment of the catalytic composition, the iridium complex is $(P(Y_4)(Y_5)(Y_6))_3Ir\ (H)_n(BY)_{3-n}$ wherein $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; n is 0, 1, or 2; and BY is a boron moiety.

In a further embodiment of the catalytic composition, the iridium complex is $(P(R_{14})(R_{15})(R_{16}))_3Ir\ (H)_n(BY)_{3-n}$ wherein $R_{14}$, $R_{15}$, and $R_{16}$ are each selected from the group consisting of hydrogen, linear alkyl, branched alkyl, and a carbon in a cyclic structure; n is 0, 1, or 2; and BY is a boron moiety.

In a further embodiment of the catalytic composition, the iridium complex is $(P(Y_4)(Y_5)(Y_6))_3Ir$ $(H)(R_{17})(BY)$ wherein $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; $R_{17}$ is selected from the group consisting of a linear alkyl containing 1 to 8 carbon atoms, branched alkyl containing 1 to 8 carbons, aryl, and a carbon in a cyclic structure; and BY is a boron moiety.

In a further embodiment of the catalytic composition, the iridium complex is $(P(R_{14})(R_{15})(R_{16}))_3Ir$ $(H)(R_{17})(BY)$ wherein $R_{14}$, $R_{15}$, and $R_{16}$ are each selected from the group consisting of hydrogen, linear alkyl, branched alkyl, and a carbon in a cyclic structure; $R_{17}$ is selected from the group consisting of a linear alkyl containing 1 to 8 carbon atoms, branched alkyl containing 1 to 8 carbons, aryl, and a carbon in a cyclic structure; and BY is a boron moiety.

In a further embodiment of the catalytic composition, the iridium complex is $\{(PY_7P)Ir(BY)_3\}_2(\mu_2\text{-}(PY_7P))$ wherein BY is a boron moiety; ($PY_7P$) is $R_{18}R_{19}P$—$Y_7$—$PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

In a further embodiment of the catalytic composition, the iridium complex is $(PY_7P)(P(Y_4)(Y_5)(Y_6))Ir(BY)_3$ wherein BY is a boron moiety; $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and ($PY_7P$) is $R_{18}R_{19}P$—$Y_7$—$PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

In a further embodiment of the catalytic composition, the iridium complex is $(PY_7P)(P(R_{14})(R_{15})(R_{16}))Ir(BY)_3$ wherein BY is a boron moiety; $R_{14}$, $R_{15}$, and $R_{16}$ are each selected from the group consisting of hydrogen, linear alkyl, branched alkyl, and a carbon in a cyclic structure; ($PY_7P$) is $R_{18}R_{19}P$—$Y_7$—$PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

In a further embodiment of the catalytic composition, the iridium complex is $\{(P^\frown P)Ir(BY)_3\}_2(\mu_2\text{-}(P^\frown P))$ wherein BY is a boron moiety and wherein $(P^\frown P)$ is of the formula

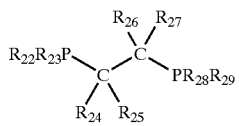

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

In a further embodiment of the catalytic composition, the iridium complex is $(P^\frown P)(P(Y_4)(Y_5)(Y_6))Ir(BY)_3$ wherein BY is a boron moiety; $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and wherein $(P^\frown P)$ is of the formula

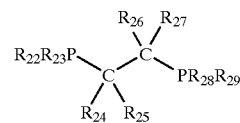

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

In a further embodiment of the catalytic composition, the iridium complex is $(P^\frown P)(P(R_{14})(R_{15})(R_{16}))Ir(BY)_3$ wherein BY is a boron moiety; $R_{14}$, $R_{15}$, and $R_{16}$ are each selected from the group consisting of hydrogen, linear alkyl, branched alkyl, and a carbon in a cyclic structure; and wherein $(P^\frown P)$ is of the formula

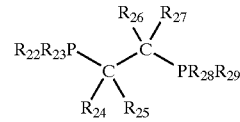

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

In a further embodiment of the catalytic composition, the iridium complex is $(PY_7P)Ir(BY)_3$ wherein BY is a boron moiety; and ($PY_7P$) is $R_{18}R_{19}P$—$Y_7$—$PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

In a further embodiment of the catalytic composition, the iridium complex is $(P^\frown P)Ir(BY)_3$ wherein BY is a boron moiety and wherein $(P^\frown P)$ is of the formula

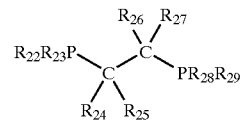

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

In a further embodiment of the catalytic composition, the iridium complex is $(P(Y_4)(Y_5)(Y_6))_4Ir(BY)$ wherein $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and BY is a boron moiety.

In a further embodiment of the catalytic composition, the iridium complex is $(P(R_{14})(R_{15})(R_{16}))_4Ir(BY)$ wherein $R_{14}$, $R_{15}$, and $R_{16}$ are each selected from the group consisting of hydrogen, linear alkyl, branched alkyl, and a carbon in a cyclic structure; and BY is a boron moiety.

In a further embodiment of the catalytic composition, the iridium complex is $(PY_7P)(P(Y_4)(Y_5)(Y_6))_2Ir(BY)$ wherein BY is a boron moiety; $Y_4$, $Y_5$, and $Y_6$ are each selected from the group consisting of hydrogen, halide, alkyl, aryl, alkoxide (—$O(R_{11})$), and amide (—$N(R_{12})(R_{13})$) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and $(PY_7P)$ is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

In a further embodiment of the catalytic composition, the iridium complex is $(P^\frown P)(P(Y_4)(Y_5)(Y_6))_2Ir(BY)$ wherein BY is a boron moiety; $Y_4$, $Y_5$, and $Y_6$ are each selected from the group consisting of hydrogen, halide, alkyl, aryl, alkoxide (—$O(R_{11})$), and amide (—$N(R_{12})(R_{13})$) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and wherein $(P^\frown P)$ is of the formula

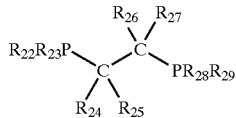

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

In a further embodiment of the catalytic composition, the iridium complex is $(PY_7P)(P(R_{14})(R_{15})(R_{16}))_2Ir(BY)$ wherein BY is a boron moiety; $R_{14}$, $R_{15}$, and $R_{16}$ are each selected from the group consisting of hydrogen, linear alkyl, branched alkyl, and a carbon in a cyclic structure; $(PY_7P)$ is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

In a further embodiment of the catalytic composition, the iridium complex is $(P^\frown P)(P(R_{14})(R_{15})(R_{16}))_2Ir(BY)$ wherein BY is a boron moiety; $R_{14}$, $R_{15}$, and $R_{16}$ are each selected from the group consisting of hydrogen, linear alkyl, branched alkyl, and a carbon in a cyclic structure; and wherein $(P^\frown P)$ is of the formula

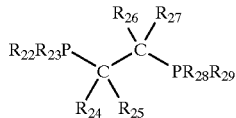

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

In a further embodiment of the catalytic composition, the iridium complex is selected from the group consisting of $(Cp^*)Ir(H)_2(Me_3P)$, $(Cp^*)Ir(H)(BPin)(Me_3P)$, $(CP^*)Ir(H)(C_6H_5)(Me_3P)$, $(Ind)Ir(COD)$, $(MesH)Ir(BPin)(B(OR)_2)$, $((R_1)_3P)_3Ir(B(OR_2)_2)_3$, $(R_1)_2P)_2Ir(BPin)_3$, $[((R_1)_2P)_3Ir((R_2O)_2B)_3]_2$, $((R_1)_3P)_4Ir(BPin)$, $((R_1)_2P)_2Ir(BPin)_3$, $(MesH)Ir(BPin)_3$, $IrCl(COD)$, and $[IrCl(COD)]_2$, wherein CP* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are each selected from the group consisting of hydrogen, linear or branched alkyl containing 1 to 8 carbons, aryl, and a carbon in a cyclic structure.

In a further embodiment of the catalytic composition, the rhodium complex is $(Cp')(P(Y_4)(Y_5)(Y_6))Rh(H)_n(BY)_{2-n}$ wherein $Y_4$, $Y_5$, and $Y_6$ are each selected from the group consisting of hydrogen, halide, alkyl, aryl, alkoxide (—$O(R_{11})$), and amide (—$N(R_{12})(R_{13})$) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; n is 0 or 1; BY is a boron moiety; and Cp' is of the formula

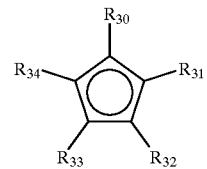

wherein $R_{30}$, $R_{31}$, $R_{32}$, $R_{33}$, and $R_{34}$ are each selected from the group consisting of hydrogen, alkyl chains, carbocyclic rings, and aryl groups.

In a further embodiment of the catalytic composition, the rhodium complex is $(Cp')(P(R_{10})(R_{11})(R_{12}))Rh(H)_n(BY)_{2-n}$ wherein $R_{10}$, $R_{11}$, and $R_{12}$ are each selected from the group consisting of hydrogen, linear alkyl, branched alkyl, and a carbon in a cyclic structure; n is 0 or 1; BY is a boron moiety; and Cp' is of the formula

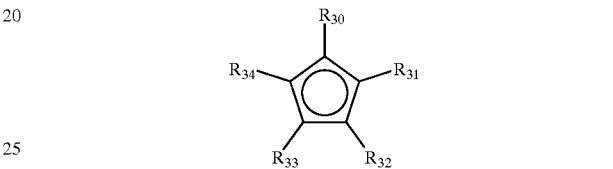

wherein $R_{30}$, $R_{31}$, $R_{32}$, $R_{33}$, and $R_{34}$ are each selected from the group consisting of hydrogen, alkyl chains, carbocyclic rings, and aryl groups.

In a preferred embodiment of the above iridium and rhodium catalytic compositions, BY is selected from the group consisting of

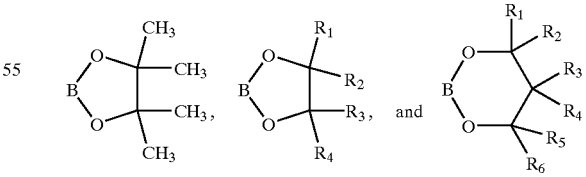

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure.

In a further embodiment of the catalytic composition, the rhodium complex is selected from the group consisting of $(Cp^*)Rh(H)_2(Me_3P)$, $(Cp^*)Rh(H)(BPin)(Me_3P)$, $(CP^*)Rh$ (H)(C$_6$H$_5$)(Me$_3$P), and (Cp*)Rh(hexamethylbenzene), wherein CP* is 1,2,3,4,5-methylcyclopentadienyl, BPin is pinacolborane, Me is methyl, H is hydrogen, and P is phosphorus.

The present invention provides a process for producing a ring-substituted arene borane which comprises reacting a ring-substituted arene with an HB organic compound in the presence of a catalytically effective amount of an iridium or rhodium complex with three or substituents, excluding hydrogen, bonded to the iridium or rhodium, to form the ring-substituted arene borane.

In a further embodiment, the present invention provides a process for producing a ring-substituted arene borane which comprises reacting a ring-substituted arene with an HB organic compound in the presence of a catalytically effective amount of an iridium or rhodium complex with three or substituents, excluding hydrogen, bonded to the iridium or rhodium and a phosphorus organic ligand, in a molar ratio of complex to ligand between about 1 to 3 and 1 to 1, wherein the ligand is at least in part bonded to the iridium or rhodium, to form the ring-substituted arene borane.

Preferably, the phosphorus organic ligand is selected from the group consisting of trimethyl phosphine (PMe$_3$), 1,2-bis(dimethylphosphino)ethane (dmpe), and 1,2-bis(diphenylphosphino)ethane (dppe).

In a further embodiment of the process, the iridium complex is (ArH)Ir(BY)$_3$ wherein ArH is selected from the group consisting of aromatic, heteroaromatic, polyaromatic, and heteropolyaromatic hydrocarbon; and BY is a boron moiety.

In a further embodiment of the process, the iridium complex is (MesH)Ir(BY)$_3$ wherein MesH is mesitylene; and BY is a boron moiety.

In a further embodiment of the process, the iridium complex is (P(Y$_4$)(Y$_5$)(Y$_6$))$_3$Ir (H)$_n$(BY)$_{3-n}$ wherein Y$_4$, Y$_5$, and Y$_6$ are each selected from the group consisting of hydrogen, halide, alkyl, aryl, alkoxide (—O(R$_{11}$)), and amide (—N(R$_{12}$)(R$_{13}$)) wherein R$_{11}$, R$_{12}$, and R$_{13}$ are each selected from the group consisting of hydrogen, linear alkyl containing 1 to 8 carbon atoms, branched alkyl containing 1 to 8 carbons, and a carbon in a cyclic structure; n is 0, 1, or 2; and BY is a boron moiety.

In a further embodiment of the process, the iridium complex is (P(R$_{14}$)(R$_{15}$)(R$_{16}$))$_3$Ir (H)$_n$(BY)$_{3-n}$ wherein R$_{14}$, R$_{15}$, and R$_{16}$ are each selected from the group consisting of hydrogen, linear alkyl, branched alkyl, and a carbon in a cyclic structure; n is 0, 1, or 2; and BY is a boron moiety.

In a further embodiment of the process, the iridium complex is (P(Y$_4$)(Y$_5$)(Y$_6$))$_3$Ir (H)(R$_{17}$)(BY) wherein Y$_4$, Y$_5$, and Y$_6$ are each selected from the group consisting of hydrogen, halide, alkyl, aryl, alkoxide (—O(R$_{11}$)), and amide (—N(R$_{12}$)(R$_{13}$)) wherein R$_{11}$, R$_{12}$, and R$_{13}$ are each selected from the group consisting of hydrogen, linear alkyl containing 1 to 8 carbon atoms, branched alkyl containing 1 to 8 carbons, and a carbon in a cyclic structure; R$_{17}$ is selected from the group consisting of a linear alkyl containing 1 to 8 carbon atoms, branched alkyl containing 1 to 8 carbons, aryl, and a carbon in a cyclic structure; and BY is a boron moiety.

In a further embodiment of the process, the iridium complex is (P(R$_{14}$)(R$_{15}$)(R$_{16}$))$_3$Ir (H)(R$_{17}$)(BY) wherein R$_{14}$, R$_{15}$, and R$_{16}$ are each selected from the group consisting of hydrogen, linear alkyl, branched alkyl, and a carbon in a cyclic structure; R$_{17}$ is selected from the group consisting of a linear alkyl containing 1 to 8 carbon atoms, branched alkyl containing 1 to 8 carbons, aryl, and a carbon in a cyclic structure; and BY is a boron moiety.

In a further embodiment of the process, the iridium complex is {(PY$_7$P)Ir(BY)$_3$}$_2$($\mu_2$-(PY$_7$P)) wherein BY is a boron moiety; (PY$_7$P) is R$_{18}$R$_{19}$P—Y$_7$—PR$_{20}$R$_{21}$ wherein R$_{18}$, R$_{19}$, R$_{20}$, and R$_{21}$ are each selected from the group consisting of hydrogen, linear alkyl containing 1 to 8 carbon atoms, branched alkyl containing 1 to 8 carbons, and a carbon in a cyclic structure, and Y$_7$ is a chain containing 1 to 12 carbons.

In a further embodiment of the process, the iridium complex is (PY$_7$P)(P(Y$_4$)(Y$_5$)(Y$_6$))Ir(BY)$_3$ wherein BY is a boron moiety; Y$_4$, Y$_5$, and Y$_6$ are each selected from the group consisting of hydrogen, halide, alkyl, aryl, alkoxide (—O(R$_{11}$)), and amide (—N(R$_{12}$)(R$_{13}$)) wherein R$_{11}$, R$_{12}$ and R$_{13}$ are each selected from the group consisting of hydrogen, linear alkyl containing 1 to 8 carbon atoms, branched alkyl containing 1 to 8 carbons, and a carbon in a cyclic structure; and (PY$_7$P) is R$_{18}$R$_{19}$P—Y$_7$—PR$_{20}$R$_{21}$ wherein R$_{18}$, R$_{19}$, R$_{20}$, and R$_{21}$ are each selected from the group consisting of hydrogen, linear alkyl containing 1 to 8 carbon atoms, branched alkyl containing 1 to 8 carbons, and a carbon in a cyclic structure, and Y$_7$ is a chain containing 1 to 12 carbons.

In a further embodiment of the process, the iridium complex is (PY$_7$P)(P(R$_{14}$)(R$_{15}$)(R$_{16}$))Ir(BY)$_3$ wherein BY is a boron moiety; R$_{14}$, R$_{15}$, and R$_{16}$ are each selected from the group consisting of hydrogen, linear alkyl, branched alkyl, and a carbon in a cyclic structure; (PY$_7$P) is R$_{18}$R$_{19}$P—Y$_7$—PR$_{20}$R$_{21}$ wherein R$_{18}$, R$_{19}$, R$_{20}$, and R$_{21}$ are each selected from the group consisting of hydrogen, linear alkyl containing 1 to 8 carbon atoms, branched alkyl containing 1 to 8 carbons, and a carbon in a cyclic structure, and Y$_7$ is a chain containing 1 to 12 carbons.

In a further embodiment of the process, the iridium complex is {(P⌒P)Ir(BY)$_3$}$_2$($\mu_2$-(P⌒P)) wherein BY is a boron moiety and wherein (P⌒P) is of the formula

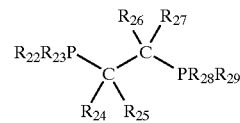

wherein R$_{22}$, R$_{23}$, R$_{24}$, R$_{25}$, R$_{26}$, R$_{27}$, R$_{28}$, and R$_{29}$ are each selected from the group consisting of alkyl chains, carbocyclic rings, and aryl groups.

In a further embodiment of the process, the iridium complex is (P⌒P)(P(Y$_4$)(Y$_5$)(Y$_6$))Ir(BY)$_3$ wherein BY is a boron moiety; Y$_4$, Y$_5$, and Y$_6$ are each selected from the group consisting of hydrogen, halide, alkyl, aryl, alkoxide (—O(R$_{11}$)), and amide (—N(R$_{12}$)(R$_{13}$)) wherein R$_{11}$, R$_{12}$, and R$_{13}$ are each selected from the group consisting of hydrogen, linear alkyl containing 1 to 8 carbon atoms, branched alkyl containing 1 to 8 carbons, and a carbon in a cyclic structure; and wherein (P⌒P) is of the formula

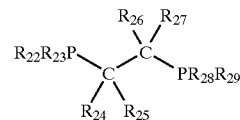

wherein R$_{22}$, R$_{23}$, R$_{24}$, R$_{25}$, R$_{26}$, R$_{27}$, R$_{28}$, and R$_{29}$ are each selected from the group consisting of alkyl chains, carbocyclic rings, and aryl groups.

In a further embodiment of the process, the iridium complex is (P⌒P)(P(R$_{14}$)(R$_{15}$)(R$_{16}$))Ir(BY)$_3$ wherein BY is a boron moiety; $R_{14}$, $R_{15}$, and $R_{16}$ are each selected from the group consisting of hydrogen, linear alkyl, branched alkyl, and a carbon in a cyclic structure; and wherein (P⌒P) is of the formula

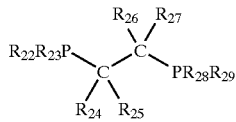

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

In a further embodiment of the process, the iridium complex is $(PY_7P)Ir(BY)_3$ wherein BY is a boron moiety; and $(PY_7P)$ is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

In a further embodiment of the process, the iridium complex is $(P⌒P)Ir(BY)_3$ wherein BY is a boron moiety and wherein (P⌒P) is of the formula

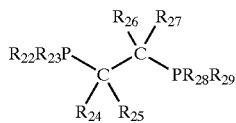

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

In a further embodiment of the process, the iridium complex is $(P(Y_4)(Y_5)(Y_6))_4Ir(BY)$ wherein $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and BY is a boron moiety.

In a further embodiment of the process, the iridium complex is $(P(R_{14})(R_{15})(R_{16}))_4Ir(BY)$ wherein $R_{14}$, $R_{15}$, and $R_{16}$ are each selected from the group consisting of hydrogen, linear alkyl, branched alkyl, and a carbon in a cyclic structure; and BY is a boron moiety.

In a further embodiment of the process, the iridium complex is $(PY_7P)(P(Y_4)(Y_5)(Y_6))_2Ir(BY)$ wherein BY is a boron moiety; $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and $(PY_7P)$ is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

In a further embodiment of the process, the iridium complex is $(P⌒P)(P(Y_4)(Y_5)(Y_6))_2Ir(BY)$ wherein BY is a boron moiety; $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and wherein (P⌒P) is of the formula

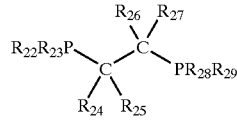

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

In a further embodiment of the process, the iridium complex is $(PY_7P)(P(R_{14})(R_{15})(R_{16}))_2Ir(BY)$ wherein BY is a boron moiety; $R_{14}$, $R_{15}$, and $R_{16}$ are each selected from the group consisting of hydrogen, linear alkyl, branched alkyl, and a carbon in a cyclic structure; $(PY_7P)$ is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

In a further embodiment of the process, the iridium complex is $(P⌒P)(P(R_{14})(R_{15})(R_{16}))_2Ir(BY)$ wherein BY is a boron moiety; $R_{14}$, $R_{15}$, and $R_{16}$ are each selected from the group consisting of hydrogen, linear alkyl, branched alkyl, and a carbon in a cyclic structure; and wherein (P⌒P) is of the formula

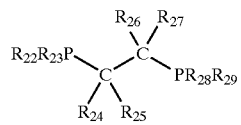

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

In a further embodiment of the process, the iridium complex is selected from the group consisting of (Cp*)Ir(H)$_2$(Me$_3$P), (Cp*)Ir(H)(BPin)(Me$_3$P), (CP*)Ir(H)(C$_6$H$_5$)(Me$_3$P), (Ind)Ir(COD), (MesH)Ir(BPin)(B(OR)$_2$), ((R$_1$)$_3$P)$_3$Ir(B(OR$_2$)$_2$)$_3$, (R$_1$)$_2$P)$_2$Ir(BPin)$_3$, [((R$_1$)$_2$P)$_3$Ir((R$_2$O)$_2$B)$_3$]$_2$, ((R$_1$)$_3$P)$_4$Ir(BPin), ((R$_1$)$_2$P)$_2$Ir(BPin)$_3$, (MesH)Ir(BPin)$_3$, IrCl(COD), and [IrCl(COD)]$_2$, wherein CP* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are each selected from the group consisting of hydrogen, linear or branched alkyl containing 1 to 8 carbons, aryl, and a carbon in a cyclic structure.

In a further embodiment of the process, the rhodium complex is $(Cp')(P(Y_4)(Y_5)(Y_6))Rh(H)_n(BY)_{2-n}$ wherein $Y_4$, $Y_5$, and $Y_6$ are each selected from the group consisting of hydrogen, halide, alkyl, aryl, alkoxide (—O($R_7$)), and amide (—N($R_8$)($R_9$)) wherein $R_7$, $R_8$, and $R_9$ are each selected from the group consisting of hydrogen, linear alkyl containing 1 to 8 carbon atoms, branched alkyl containing 1 to 8 carbons, and a carbon in a cyclic structure; n is 0 or 1; BY is a boron moiety; and Cp' is of the formula

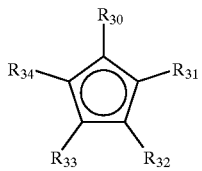

wherein $R_{30}$, $R_{31}$, $R_{32}$, $R_{33}$, and $R_{34}$ are each selected from the group consisting of hydrogen, alkyl chains, carbocyclic rings, and aryl groups.

In a further embodiment of the process, the rhodium complex is $(Cp')(P(R_{10}(R_{11})(R_{12}))Rh(H)_n(BY)_{2-n}$ wherein $R_{10}$, $R_{11}$, and $R_{12}$ are each selected from the group consisting of hydrogen, linear alkyl, branched alkyl, and a carbon in a cyclic structure; n is 0 or 1; BY is a boron moiety; and Cp' is of the formula

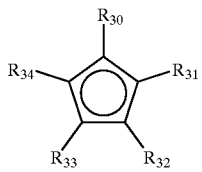

wherein $R_{30}$, $R_{31}$, $R_{32}$, $R_{33}$, and $R_{34}$ are each selected from the group consisting of hydrogen, alkyl chains, carbocyclic rings, and aryl groups.

In a preferred embodiment of the process, BY is selected from the group consisting of

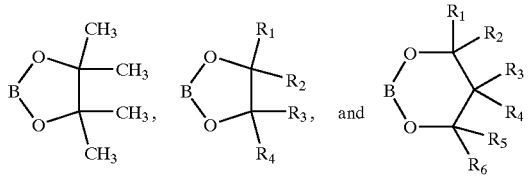

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure.

In a further embodiment of the process, the rhodium complex is selected from the group consisting of $(Cp^*)Rh(H)_2(Me_3P)$, $(Cp^*)Rh(H)(BPin)(Me_3P)$, $(CP^*)Rh(H)(C_6H_5)(Me_3P)$, and $(Cp^*)Rh(hexamethylbenzene)$, wherein $CP^*$ is 1,2,3,4,5-methylcyclopentadienyl, BPin is pinacolborane, Me is methyl, H is hydrogen, and P is phosphorus.

In a further embodiment of the process, the HB organic ligand is selected from the group consisting of $B(H)(Y_{11})(Y_{12})$ wherein $Y_{11}$ and $Y_{12}$ are each selected from the group consisting of hydrogen, halide, alkyl, aryl, alkoxide (—O($R_7$)), and amide (—N($R_8$)($R_9$)) wherein $R_7$, $R_8$, and $R_9$ are each selected from the group consisting of hydrogen, linear alkyl containing 1 to 8 carbon atoms, branched alkyl containing 1 to 8 carbons, and a carbon in a cyclic structure; $(B(H)(Y_{13}-Y_{14}-Y_{15}))$ wherein $Y_{13}$ and $Y_{15}$ are each selected from the group consisting of alkyl, aryl, oxygen, and nitrogen and $Y_{14}$ is a chain containing 1 to 12 carbon atoms;

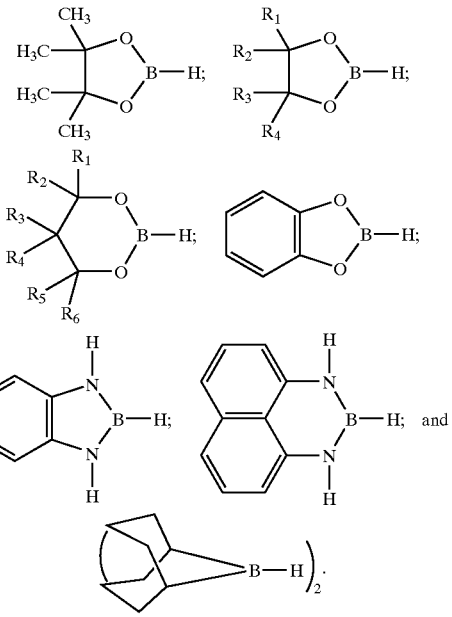

The present invention further provides a ring-substituted arene borane of the formula

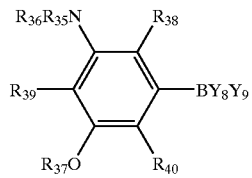

wherein $Y_8$ and $Y_9$ are each selected from the group consisting of hydrogen, halide, alkyl, aryl, alkoxide, amide, and a group containing any other element wherein the element is bound to boron; $R_{35}$, $R_{36}$, and $R_{37}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and $R_{38}$, $R_{39}$, and $R_{40}$ are each selected from the group consisting of hydrogen, halide, alkyl, aryl, alkoxide, amide, and a group containing any other element which is bound to the aromatic ring.

The present invention further provides a ring-substituted arene borane of the formula

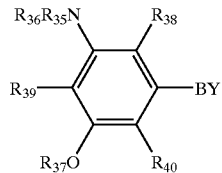

wherein $R_{35}$, $R_{36}$, and $R_{37}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and R₃₈, R₃₉, and R₄₀ are each selected from the group consisting of hydrogen, halide, alkyl, aryl, alkoxide, amide, and a group containing any other element which is bound to the aromatic ring; and BY is a boron moiety selected from the group consisting of

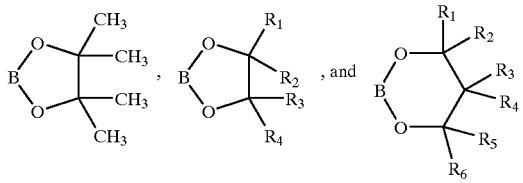

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbon atoms, aryl, and carbon within a cyclic structure.

The present invention further provides a ring-substituted arene borane of the formula

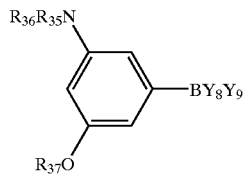

wherein $Y_8$ and $Y_9$ are each selected from the group consisting of hydrogen, halide, alkyl, aryl, alkoxide, amide, and a group containing any other element wherein the element is bound to boron; and $R_{35}$, $R_{36}$, and $R_{37}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group.

The present invention further provides a ring-substituted arene borane of the formula

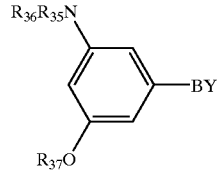

wherein $R_{35}$, $R_{36}$, and $R_{37}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and BY is a boron moiety selected from the group consisting of

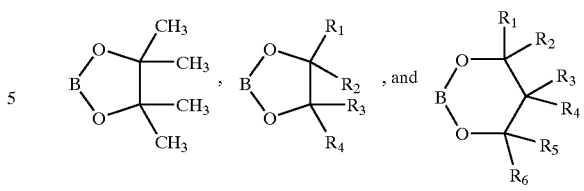

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbon atoms, aryl, and carbon within a cyclic structure.

The present invention further provides a ring-substituted arene borane of the formula

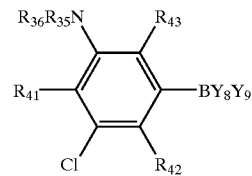

wherein $Y_8$ and $Y_9$ are each selected from the group consisting of hydrogen, halide, alkyl, aryl, alkoxide, amide, and a group containing any other element wherein the element is bound to boron; $R_{35}$ and $R_{36}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and $R_{41}$, $R_{42}$, and $R_{43}$ are each selected from the group consisting of hydrogen, halide, alkyl, aryl, alkoxide, amide, and a group containing any other element which is bound to the aromatic ring.

The present invention further provides a ring-substituted arene borane of the formula

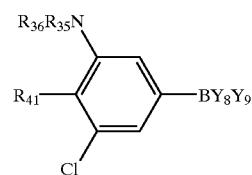

wherein $Y_8$ and $Y_9$ are each selected from the group consisting of hydrogen, halide, alkyl, aryl, alkoxide, amide, and a group containing any other element wherein the element is bound to boron; $R_{35}$ and $R_{36}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and $R_{41}$ is selected from the group consisting of halide, alkyl, aryl, alkoxide, amide, and a group containing any other element except hydrogen which is bound to the aromatic ring.

The present invention further provides a ring-substituted arene borane of the formula

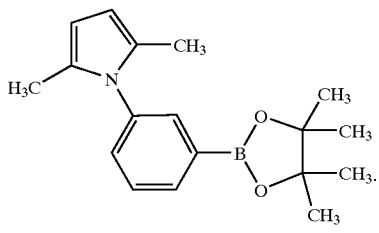

The present invention further provides a ring-substituted arene borane of the formula

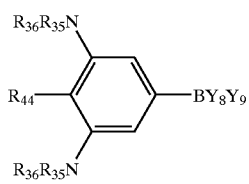

wherein $Y_8$ and $Y_9$ are each selected from the group consisting of hydrogen, halide, alkyl, aryl, alkoxide, amide, and a group containing any other element wherein the element is bound to boron; $R_{35}$ and $R_{36}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and $R_{44}$ is selected from the group consisting of alkoxide, amide, and a group containing any other element which is bound to the aromatic ring except for hydrogen or carbon.

The present invention further provides a ring-substituted arene borane of the formula

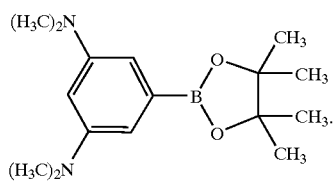

The present invention further provides a ring-substituted arene borane of the formula

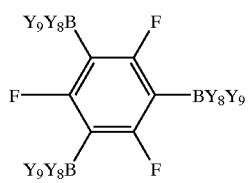

wherein $Y_8$ and $Y_9$ are each selected from the group consisting of hydrogen, halide, alkyl, aryl, alkoxide, amide, and a group containing any other element wherein the element is bound to boron.

The present invention further provides a ring-substituted arene borane of the formula

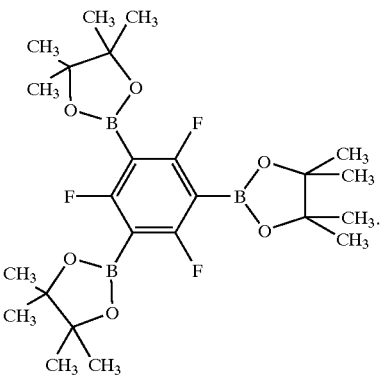

The present invention further provides a ring-substituted arene borane of the formula

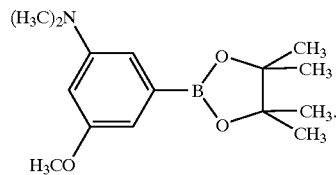

The present invention further provides a ring-substituted arene borane of the formula

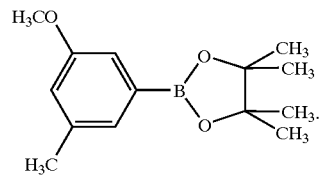

OBJECTS

It is an object of the present invention to provide a general process for synthesizing boronic esters and acids which avoids many of the limitations of the prior art processes.

A further object of the present invention is to provide a general process for synthesizing boronic esters and acids by metal catalyzed activations of C—H bonds in hydrocarbon feedstocks and B—H bonds in boron reagents to produce novel B—C bonds with hydrogen as the sole byproduct of the process.

A further still object of the present invention is to provide catalysts which can be used for the general process for synthesizing boronic esters and acids.

These and other objects of the present invention will become increasingly apparent with reference to the following drawings and preferred embodiments.

DETAILED DESCRIPTION OF THE DRAWINGS

FIG. 1 shows the formulas for precatalysts 1 to 15. CP* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are each selected from the group consisting of hydrogen, linear or branched alkyl containing 1 to 8 carbons, aryl, and a carbon in a cyclic structure.

Figure 2:
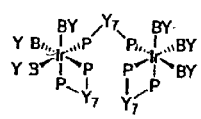
Figure 2:
Figure 2:
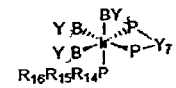
Figure 2:
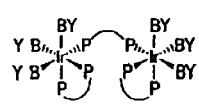
Figure 2:
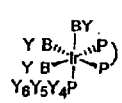
Figure 2:
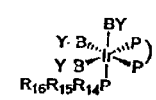
Figure 2:
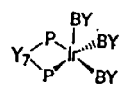
Figure 2:
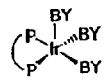
Figure 2:
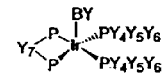
Figure 2:
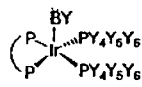
Figure 2:
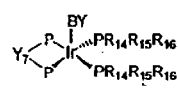
Figure 2:
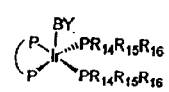

FIG. 2 shows the formulas for precatalysts 16 to 27. $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; $R_{14}$, $R_{15}$, and $R_{16}$ are each selected from the group consisting of hydrogen, linear alkyl, branched alkyl, and a carbon in a cyclic structure; ($PY_7P$) is $R_{18}R_{19}P$—$Y_7$—$PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons; ((P⌢P) is of the formula

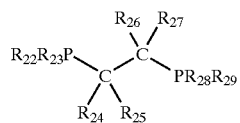

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups; and BY is a boron moiety.

DETAILED DESCRIPTION OF THE INVENTION

All patents, patent applications, provisional patent applications, government publications, government regulations, and literature references cited in this specification are hereby incorporated herein by reference in their entirety. In case of conflict, the present description, including definitions, will control.

The present invention provides catalysts comprising iridium (Ir) or rhodium (Rh) in a complex with three or more substituents, excluding hydrogen, bonded to the Ir or Rh and a phosphorus organic ligand, which is at least in part bonded to the Ir or Rh and processes for forming B—C bonds between boranes and sp2-hybridized C—H bonds to produce organoboron complexes such as ring-substituted arenes (or aryl boronate esters and acids) according to the process shown in Scheme 1.

Scheme 1

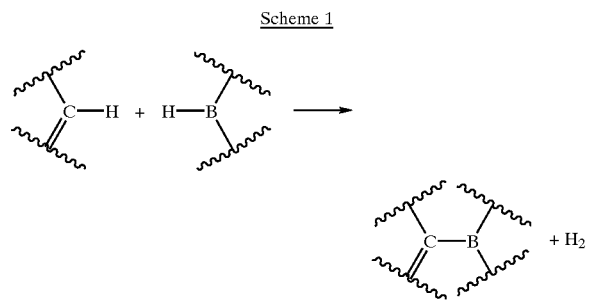

The direct route to aryl boronate esters and acids using the catalysts and process of the present invention is particularly useful for producing ring-substituted arene boranes (aryl boronic esters and acids) which are versatile transfer reagents in organic chemistry. The boron in these transfer reagents serves as a mask for a broad range of heteroatoms and functional groups. Some of the most remarkable and broadly used applications of organoboron chemistry are catalytic cross-coupling check reactions of C—B and C—X (X is Cl, Br, I) groups which yield new C—C bonds as shown in scheme 2. In addition, the present invention provides novel boranes and novel organoborane complexes.

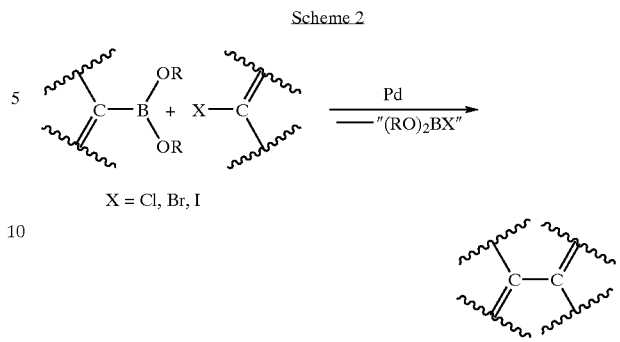

The novel boranes and organoborane complexes are particularly useful in the pharmaceutical industry as key building blocks for drug manufacturing and as versatile reagents for high-throughput parallel synthesis in drug discovery. In addition, the borane and organoboron complexes are useful for the manufacture of chemical sensing and high-performance specialty polymers.

The B—C bond-forming reactions between boranes and sp2-hybridized C—H bonds are catalyzed by the catalysts of the present invention which comprise Ir and Rh in a complex with three or more substituents, excluding hydrogen, bonded to the Ir or Rh and a phosphorus organic ligand, which is at least in part bonded to the Ir or Rh. Preferably, the catalysts comprise iridium or rhodium in a complex with three or more substituents, excluding hydrogen, bonded to the iridium or rhodium and an organic ligand selected from the group consisting of a phosphorus organic ligand, an organic amine, an imine, a nitrogen heterocycle, and an ether in a molar ratio between about 1 to 3 and 1 to 1, wherein the ligand is at least in part bonded to the iridium or rhodium. Effective precatalysts can be grouped into two families: those that contain cyclopentadienyl (Cp*, $C_5R_5$ wherein R is $CH_3$) or indenyl (Ind, $C_9R_7$ wherein R is H) ligands and those that contain phosphine ligands. Included are compounds that contain both the Cp* and the Ind ligands and the phosphine ligands.

Preferably, the catalytic composition comprising iridium comprises one of the following: (ArH)Ir(BY)$_3$ wherein ArH is selected from the group consisting of aromatic, heteroaromatic, polyaromatic, and heteropolyaromatic hydrocarbon and wherein BY is a boron moiety; (MesH)Ir(BY)$_3$ wherein MesH is mesitylene and wherein BY is a boron moiety; (P($Y_4$)($Y_5$)($Y_6$))$_3$Ir (H)$_n$(BY)$_{3-n}$ wherein $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure, wherein n is 0, 1, or 2, and wherein BY is a boron moiety; (P($R_{14}$)($R_{15}$)($R_{16}$))$_3$Ir (H)$_n$(BY)$_{3-n}$ wherein $R_{14}$, $R_{15}$, and $R_{16}$ are each selected from the group consisting of hydrogen, linear alkyl, branched alkyl, and a carbon in a cyclic structure, wherein n is 0, 1, or 2, and wherein BY is a boron moiety; (P($Y_4$) ($Y_5$)($Y_6$))$_3$Ir (H)($R_{13}$)(BY) wherein $Y_4$, $Y_5$, and $Y_6$ are as above, wherein $R_{13}$ is selected from the group consisting of a linear alkyl containing 1 to 8 carbon atoms, branched alkyl containing 1 to 8 carbons, aryl, and a carbon in a cyclic structure, and wherein BY is a boron moiety; (P($R_{14}$)($R_{15}$) ($R_{16}$))$_3$Ir (H)($R_{17}$)(BY) wherein $R_{14}$, $R_{15}$, and $R_{16}$ are as above; $R_{17}$ is as above, and wherein BY is a boron moiety; {(PY$_7$P)Ir(BY)$_3$}$_2$($\mu_2$-(PY$_7$P)) (16) wherein BY is a boron moiety, wherein (PY₇P) is $R_{18}R_{19}P$—$Y_7$—$PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and wherein $Y_7$ is a chain containing 1 to 12 carbons; $(PY_7P)(P(Y_4)(Y_5)(Y_6))Ir(BY)_3$ (17) wherein BY is a boron moiety, wherein $Y_4$, $Y_5$, and $Y_6$ are as above, and wherein (PY₇P) is as above; $(PY_7P)(P(R_{10})(R_{11})(R_{12}))Ir(BY)_3$ (18) wherein BY is a boron moiety, wherein $R_{14}$, $R_{15}$, and $R_{16}$ are as above, wherein (PY₇P) is as above; $\{(P^\frown P)Ir(BY)_3\}_2(\mu_2\text{-}(P^\frown P))$ (19) wherein BY is a boron moiety and wherein (P⌢P) is of the formula

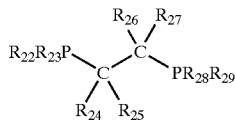

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups; $(P^\frown P)(P(Y_4)(Y_5)(Y_6))Ir(BY)_3$ (20) wherein BY is a boron moiety, wherein $Y_4$, $Y_5$, and $Y_6$ are as above, and wherein (P⌢P) is as above; $(P^\frown P)(P(R_{14})(R_{15})(R_{16}))Ir(BY)_3$ (21) wherein BY is a boron moiety, wherein $R_{14}$, $R_{15}$, and $R_{16}$ are as above, and wherein (P⌢P) is as above; $(PY_7P)Ir(BY)_3$ (22) wherein BY is a boron moiety, and wherein and (PY₇P) is as above; $(P^\frown P)Ir(BY)_3$ (23) wherein BY is a boron moiety, and wherein (P⌢P) is as above; $(P(Y_4)(Y_5)(Y_6))_4Ir(BY)$ wherein $Y_4$, $Y_5$, and $Y_6$ are as above and BY is a boron moiety; $(P(R_{14})(R_{15})(R_{16}))_4Ir(BY)$ wherein $R_{14}$, $R_{15}$, and $R_{16}$ are as above and BY is a boron moiety; $(PY_7P)(P(Y_4)(Y_5)(Y_6))_2Ir(BY)$ (24) wherein BY is a boron moiety, wherein $Y_4$, $Y_5$, and $Y_6$ are above, and wherein (PY₇P) is as above; $(P^\frown P)(P(Y_4)(Y_5)(Y_6))_2Ir(BY)$ (25) wherein BY is a boron moiety, wherein $Y_4$, $Y_5$, and $Y_6$ are as above, and wherein (P⌢P) is as above; $(PY_7P)(P(R_{14})(R_{15})(R_{16}))_2Ir(BY)$ (26) wherein BY is a boron moiety, $R_{14}$, $R_{15}$, and $R_{17}$ are as above, and wherein (PY₇P) is as above; $(P^\frown P)(P(R_{14})(R_{15})(R_{16}))_2Ir(BY)$ (27) wherein BY is a boron moiety, wherein $R_{14}$, $R_{15}$, and $R_{16}$ are as above, and wherein (P⌢P) is as above.

Examples of catalytic compositions comprising iridium include those selected from the group consisting of $(Cp^*)Ir(H)_2(Me_3P)$ (1), $(Cp^*)Ir(H)(BPin)(Me_3P)$ (2), $(CP^*)Ir(H)(C_6H_5)(Me_3P)$ (3), $(Ind)Ir(COD)$ (8), $(MesH)Ir(BPin)(B(OR)_2)$ (9), $((R_1)_3P)_3Ir(B(OR_2)_2)_3$ (10), $(R_1)_2P)_2Ir(BPin)_3$ (11), $[((R_1)_2P)_3Ir((R_2O)_2B)_3]_2$ (12), $((R_1)_3P)_4Ir(BPin)$ (13), $((R_1)_2P)_2Ir(BPin)_3$ (14), $(MesH)Ir(BPin)_3$ (9 wherein $B(OR)_2$ is BPin), $IrCl(COD)$ (15) and $[IrCl(COD)]_2$, wherein CP* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are each selected from the group consisting of hydrogen, linear or branched alkyl containing 1 to 8 carbons, aryl, and a carbon in a cyclic structure.

Preferably, the catalytic composition comprising rhodium comprises one of the following: $(Cp')(P(Y_4)(Y_5)(Y_6))Rh(H)_n(BY)_{2-n}$ wherein $Y_4$, $Y_5$, and $Y_6$ are as above, wherein n is 0 or 1, wherein BY is a boron moiety, and wherein Cp' is of the formula

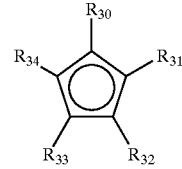

wherein $R_{30}$, $R_{31}$, $R_{32}$, $R_{33}$, and $R_{34}$ are each selected from the group consisting of hydrogen, alkyl chains, carbocyclic rings, and aryl groups; and $(Cp')(P(R_{14}(R_{15})(R_{16}))Rh(H)_n(BY)_{2-n}$ wherein $R_{14}$, $R_{15}$, and $R_{16}$ are as above; n is 0 or 1, wherein BY is a boron moiety; and wherein Cp' is as above.

Examples of catalytic compositions comprising rhodium include those selected from the group consisting of $(Cp^*)Rh(H)_2(Me_3P)$ (4), $(Cp^*)Rh(H)(BPin)(Me_3P)$ (5), $(CP^*)Rh(H)(C_6H_5)(Me_3P)$ (6), and $(Cp^*)Rh(hexamethylbenzene)$ (7), wherein CP* is 1,2,3,4,5-methylcyclopentadienyl, BPin is pinacolborane, Me is methyl, H is hydrogen, and P is phosphorus.

In the above catalytic compositions, preferably the BY boron moiety selected from the group consisting of

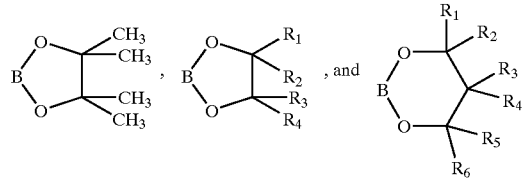

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure. FIGS. 1 and 2 show the structures of precatalysts 1 to 15 and 16 to 27, respectively.

While the precatalysts can under particular reaction conditions catalyze the borylation of particular ring-substituted arenes, the reactions proceed more efficiently when an organic ligand such as phosphine ligands (phosphorus organic ligands) are included in the reaction mixture. The addition of phosphine ligands to the reaction generates active catalysts which can produce ring-substituted arene borones (aryl boronate esters and acids) with low catalyst loading. The fact that phosphine-containing species can catalyze borylation is important because numerous phosphines are commercially available. Furthermore, the selectivities of the borylation can be altered as a function of the phosphine ligand that is added. Examples of phosphine ligands include, but are not limited to, trimethyl phosphine $(PMe_3)$, 1,2-bis(dimethylphosphino)ethane (dmpe), and 1,2-bis(diphenylphosphino)ethane (dppe).

For example, precatalyst 8 can be obtained in two high-yielding steps from the common iridium starting material, $IrCl_3(H_2O)_x$. Precatalyst 9 can be prepared by reacting 8 with approximately 5 equivalents of pinacolborane (HBPin) in mesitylene solvent. It was discovered that commercially available precatalyst 15 will also catalyze borylations. While all of the precatalysts have similar activities for many substrates, borylations of particular arenes exhibit a remarkable precatalyst dependence.

In the absence of phosphine ligands, compound 8 catalyzes the borylation of benzene by HBPin, but relatively high catalyst loading and long reaction times are required to prepare PhBPin in reasonable yields. At temperatures above 80° C., decomposition to Ir metal occurs, which halts catalysis. Compound 9 is not effective in catalysis without the addition of phosphine.

Addition of phosphine ligands to solutions of compound 8 and 9 generates active catalysts for the production of aryl boronic esters with low catalyst loading as illustrated for the examples in FIG. 1. The fact that phosphine-containing species can catalyze borylation is important because numerous phosphines are commercially available. Consequently, the selectivities can be altered as a function of the phosphine that is added.

Another virtue of the present invention is that a broad range of heteroatoms and functional groups are inert under borylation conditions as shown in Scheme 3.

Scheme 3

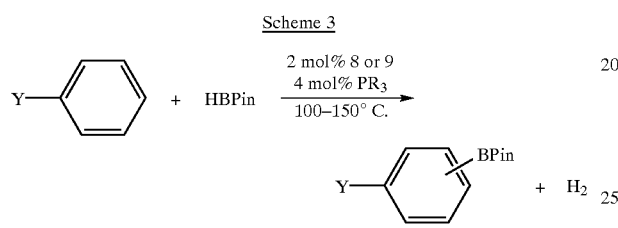

Y=F, Cl, Br, Alkyl, OR, $NMe_2$, $CF_3$, C=O($NR_2$), C=O(OR)

Given that Grignard reagents react with several of these groups and Pd catalyzes the formation of ArBPin from ArBr and HBPin, the functional group tolerance for the Ir-catalyzed chemistry is remarkable. Under appropriate conditions, even iodobenzene can be borylated without iodide reduction. In this instance, no conversion was observed when using precatalyst 8, whereas precatalyst 9 gives the borylated products in 95% yield as shown in Scheme 4.

Scheme 4

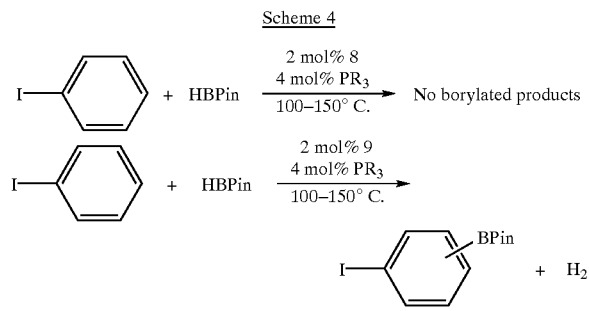

Therefore, the present substrate compatibility, which is already remarkably broad, is expected to expand with further improvements to the present invention.

For monosubstituted arenes, mixtures of meta and para borylated products are obtained. In contrast to the known Rh complexes that catalyze aromatic borylation, the meta:para ratio deviates significantly from 2:1. For most substrates, this ratio exceeds 3:1 and data for anisole are shown in Table 1.

TABLE 1

Isomer distributions for catalytic borylations of anisole

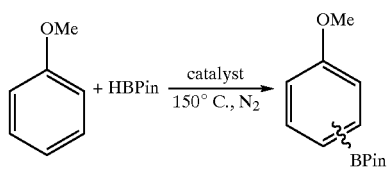

| Entry | Catalyst | Temp (° C.) | Time (h) | o:m:p |
|---|---|---|---|---|
| 1 | 2 mol % 8/2 $PMe_3$ | 150 | 29 | 9:74:17 |
| 2 | 2 mol % 9/2 $PMe_3$ | 150 | 41 | 8:75:17 |
| 3 | 2 mol % 8/dppe | 150 | 22 | 3:76:21 |
| 4 | 2 mol % 9/dppe | 150 | 51 | 3:78:20 |
| 5 | 2 mol % 8/dppe | 100 | 22 | 2:80:18 |
| 6 | 2 mol % 3/dppe | 100 | 18 | 2:80:18 |
| 7 | 2 mol % 9 | 150 | 3 | 12:53:36[a] |
| 8 | 2 mol % 8/$PMe_3$ | 150 | 29 | 2:57:40 |
| 9 | 2 mol % 9/$PMe_3$ | 150 | 40 | 3:67:30 |

[a]Low conversion.
o is ortho, m is meta, and p is para.
Dppe is 1,2-bis(diphenylphosphino)ethane It is noteworthy that the para isomer is more favored for entries 7 and 8, where the meta:para ratio is significantly less than 2:1. These data show that while there is a steric bias against ortho borylation, the meta:para ratio is sensitive to the type and amount of phosphine ligands that are added. For dppe, the activity at 100° C. is relatively high, and the reaction is complete in less time than at 150° C.

With the exception of F, and amide functional groups in some Rh catalyzed reactions, borylation at positions that are ortho to functional groups are avoided. Thus, 1,3-substituted aromatics can be selectively borylated at the 5' position. This is the hardest position to selectively activate by traditional aromatic substitution chemistry and for electron rich arenes, there are no general methods for preparing derivatives from the 1,3-substituted arenes.

Furthermore, multiple borylation of 1,3-substituted arenes does not occur to a significant extent, which means that equimolar quantities of borane and arene give aromatic boronic esters in high yield in the absence of solvent. Substrates that have been successfully converted to boronate esters under these conditions are shown in scheme 5.

Scheme 5

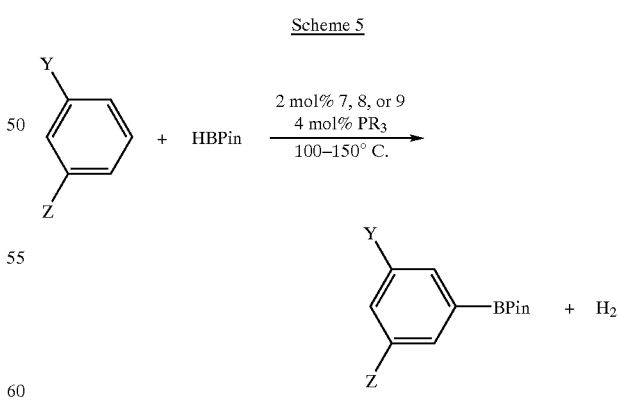

Y,Z+ Cl, Br, Alkyl, OR, $NMe_2$, $CF_3$, C=O($NR_2$), C=O(OR)

For fluorinated benzenes, the borylation at ortho positions occurs readily. Hence, $C_6HF_5$ and 1,3,5-trifluorobenzene give mono and triborylated products, respectively, as shown in Scheme 6.

Scheme 6

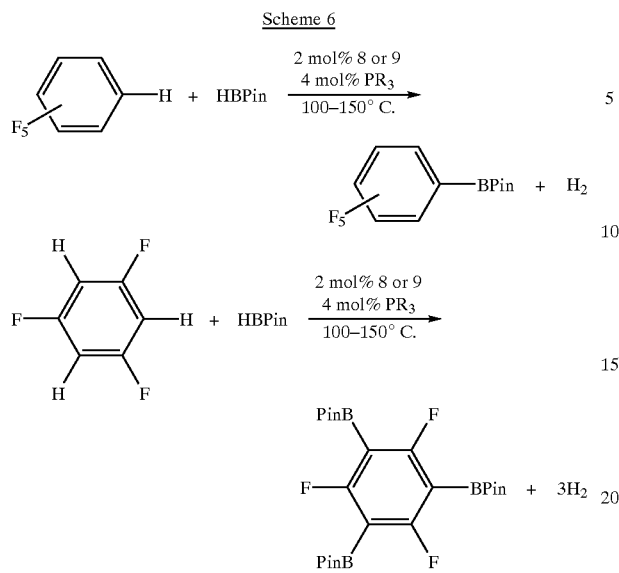

It is noteworthy that present Rh catalysts are not compatible with halide functionalities and substantial quantities of dehalogenated and diborylated products are observed. We extended the chemistry to five-membered rings and heterocycles as shown by the borylation of a protected pyrrole and 2,6-lutidine in Scheme 7

Scheme 7

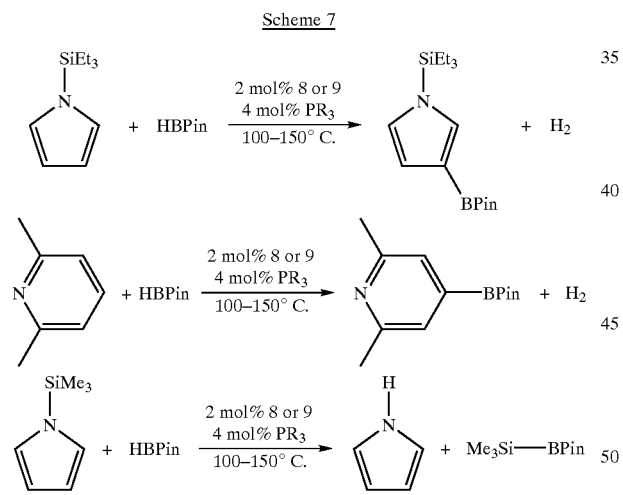

Interestingly, it was found that $(CH_3)_3Si$—BPin is produced catalytically when the C—H activation of N-trimethylsilyl pyrrole was attempted. Since Si—B reagents interesting chemistry, this provides a very simple route as compared to most of the known methods.

Lastly, we have demonstrated that aromatic borylation of one aromatic substrate and subsequent coupling with a second sp²-hybridized halocarbon can be achieved in one pot as shown in Scheme 8. One extension of this concept is the development of a catalyst kit that can be used for general couplings in drug discovery applications.

Scheme 8

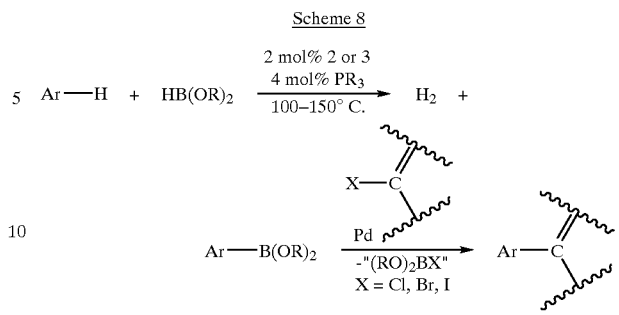

The following ring-substituted arene boranes have been synthesized according to the process of the present invention:

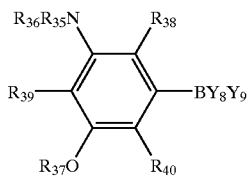

wherein $Y_8$ and $Y_9$ are each selected from the group consisting of hydrogen, halide, alkyl, aryl, alkoxide, amide, and a group containing any other element wherein the element is bound to boron; $R_{35}$, $R_{36}$, and $R_{37}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and $R_{38}$, $R_{39}$, and $R_{40}$ are each selected from the group consisting of hydrogen, halide, alkyl, aryl, alkoxide, amide, and a group containing any other element which is bound to the aromatic ring;

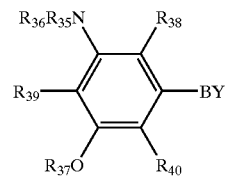

wherein $R_{35}$, $R_{36}$, and $R_{37}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and $R_{38}$, $R_{39}$, and $R_{40}$ are each selected from the group consisting of hydrogen, halide, alkyl, aryl, alkoxide, amide, and a group containing any other element which is bound to the aromatic ring; and wherein $Y_8$ and $Y_9$ are each selected from the group consisting of hydrogen, halide, alkyl, aryl, alkoxide, amide, and a group containing any other element wherein the element is bound to boron; and $R_{35}$, $R_{36}$, and $R_{37}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group;

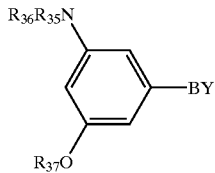

wherein $R_{35}$, $R_{36}$, and $R_{37}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and BY is a boron moiety;

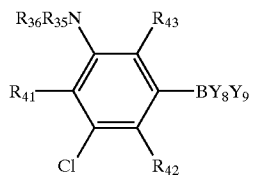

wherein $Y_8$ and $Y_9$ are each selected from the group consisting of hydrogen, halide, alkyl, aryl, alkoxide, amide, and a group containing any other element wherein the element is bound to boron; $R_{35}$ and $R_{36}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and $R_{41}$, $R_{42}$, and $R_{43}$ are each selected from the group consisting of hydrogen, halide, alkyl, aryl, alkoxide, amide, and a group containing any other element which is bound to the aromatic ring;

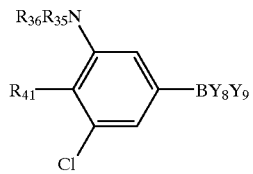

wherein $Y_8$ and $Y_9$ are each selected from the group consisting of hydrogen, halide, alkyl, aryl, alkoxide, amide, and a group containing any other element wherein the element is bound to boron; $R_{35}$ and $R_{36}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and $R_{41}$ is selected from the group consisting of halide, alkyl, aryl, alkoxide, amide, and a group containing any other element except hydrogen which is bound to the aromatic ring;

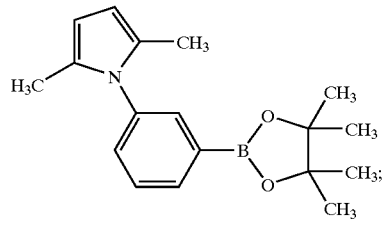

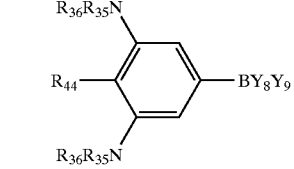

wherein $Y_8$ and $Y_9$ are each selected from the group consisting of hydrogen, halide, alkyl, aryl, alkoxide, amide, and a group containing any other element wherein the element is bound to boron; $R_{35}$ and $R_{36}$ are each selected from the group consisting of hydrogen, linear alkyl containing 1 to 8 carbon atoms, branched alkyl containing 1 to 8 carbon atoms, aryl, carbon within a cyclic structure, a silicon containing moiety wherein the silicon is bound to a nitrogen or oxygen which is bound to the aromatic ring, amine protecting group, and alcohol protecting group; and $R_{44}$ is selected from the group consisting of alkoxide, amide, and a group containing any other element which is bound to the aromatic ring except for hydrogen or carbon;

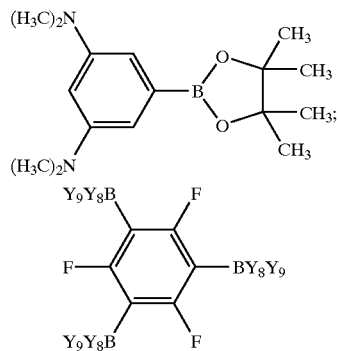

wherein $Y_8$ and $Y_9$ are each selected from the group consisting of hydrogen, halide, alkyl, aryl, alkoxide, amide, and a group containing any other element wherein the element is bound to boron;

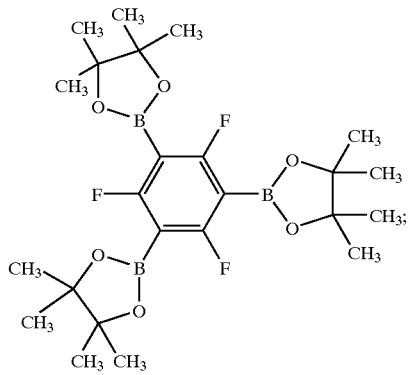

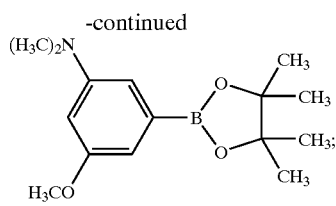

and,

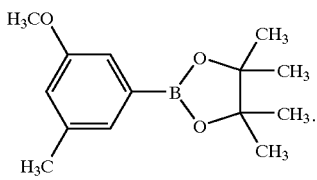

In the above ring-substituted arene boranes, BY is a boron moiety selected from the group consisting of

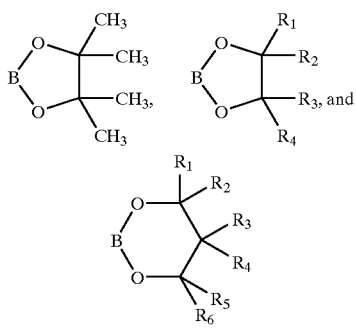

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbon atoms, aryl, and carbon within a cyclic structure.

The process and catalysts of the present invention for making ring-substituted arene boranes (aryl boronate esters and acids) avoid many of the limitations of the prior art because (1) the reactions can be carried out in neat substrates, thereby avoiding ethereal solvents, (2) since the C—H bonds are selectively activated, halogenation of arenes and conversions to Grignard or organolithium reagents are eliminated, (3) the only byproducts are hydrogen, which is easily removed, and the catalyst, which is present in low concentrations, can be recovered, (4) the process of the present invention tolerates a broad range of functional groups, (6) active catalysts are generated from common precursors and selectivities can be altered by adding commercially available ligands such as alkyl phosphines, (7) particular substitution patterns which are notoriously difficult to achieve using prior art aromatic substitution chemistry can be obtained in one step starting from inexpensive starting materials, and (8) Ir metal is relatively inert, Ir complexes generally have low toxicity, and Ir metal recovered from the reactions can be recovered from the reaction waste and recycled. Furthermore, the process can be used to make chiral borylated compounds.

The following examples are intended to promote a further understanding of the present invention.

EXAMPLE 1

This example shows the preparation of Ir(MesH)(Bin)$_3$ 9 from (Indenyl)Ir(COD) 8 and excess HBPin in mesitylene.

(Indenyl)Ir(COD) 8 (2.54 g, 6.11 mmol) and HBPin (3.91 g, 30.6 mmol) were dissolved in mesitylene (32 mL). The solution was then transferred to two glass bombs. The light brown solutions were then heated at 75° C. for 64 h. The reaction mixture turned to dark brown after 24 h at 75° C. The solutions were combined again. Mesitylene was removed by high vacuum leaving a viscous dark brown oil. The reaction mixture was then tritrated with hexamethyldisiloxane (3×2 mL). After filtration and washed with cold hexamethyldisiloxane, a white solid was obtained (797 mg, 19%). (MesH)Ir(BPin)$_3$ 9: $^1$H NMR (C$_6$D$_6$) δ 1.33 (s, 36H, 3 BO$_2$C$_6$H$_{12}$), 2.23 (s, 9H, 3 CH$_3$), 5.62 (s, 3H, 3 CH). $^{11}$B NMR (C$_6$D$_6$) δ 32.5. $^{13}$C NMR (C$_6$D$_6$) δ 19.68, 25.73, 80.95, 96.97, 118.05. Elemental analysis for C$_{27}$H$_{48}$B$_3$IrO$_6$ calcd. C, (46.77%); H, (6.98%); N, (0.00%).

Found C, (47.13%); H, (7.18%); N, (0.02%).

EXAMPLE 2

This example shows the synthesis of precatalyst 12 in a NMR reaction.

(MesH)Ir(BPin)$_3$ 9 (10 mg, 0.014 mmol) was dissolved in C$_6$D$_6$ (400 μL) and dmpe solution (0.14 M in C$_6$D$_6$, 100 μL, 0.014 mmol) was added. The reaction mixture was transferred to a J. Young NMR tube. After 36 h at room temperature, 12 was observed in $^1$H, $^{11}$B, and $^{31}$P NMR. $^1$H NMR (C$_6$D$_6$) δ 1.30 (s, 24H, BO$_2$C$_6$H$_{12}$, 1.33 (s, 48H, BO$_2$C$_6$H$_{12}$, 1.34 (unresolved d, 12H), 1.39 (d, $^2J_{HP}$=4.5 Hz, 24H), 1.68 (d, $^2J_{HP}$=6.3 Hz, 4H), 1.73 (d, $^2J_{HP}$=6.6 Hz, 4H), 1.83 (unresolved d, 4H). $^{11}$B NMR (C$_6$D$_6$) δ 32.4 (br s). $^{31}$P NMR (C$^6$D$^6$) δ −50.54 (unresolved t, 2 P), −10.85 (unresolved d, 4 P).

EXAMPLE 3

This example shows the synthesis of precatalyst 11 in a NMR reaction.

(MesH)Ir(BPin)$_3$ 9 (10 mg, 0.014 mmol) and bis-(di-tert-butylphosphino)ethane (dtBupe) (4.5 mg, 0.014 mmol) were dissolved in C$_6$H$_{12}$ (500 μL) and transferred to a J. Young NMR tube. After 16 h at room temperature, 11 was observed in $^1$H, $^{11}$B and $^{31}$P NMR. $^1$H NMR (C$_6$H$_{12}$) δ 1.19 (s, 36H, BO$_2$C$_6$H$_{12}$), 1.28 (d, $^3J_{HP}$=12.0 Hz, 36H, $^t$Bu$_2$P), 1.84 (d, $^2J_{HP}$=10.7 Hz, 4H, PCH$_2$CH$_2$P). $^{11}$B NMR (C$_6$H$_{12}$) δ 33.5 (br s). $^{31}$P NMR (C$_6$H$_{12}$) δ 894.89.

EXAMPLE 4

This example shows the synthesis of Preparation of fac-Ir(PMe$_3$)$_3$(BPin)$_3$.

PMe$_3$ (220 mg, 2.9 mmol) diluted in 2 mL C$_6$H$_6$ was added into a vial which was charged with (MesH)Ir(BPin)$_3$ (400 mg, 0.58 mmol) in 4 mL C$_6$H$_6$. The reaction mixture was stirred at ambient temperature for 30 minutes and the solvent was removed away under vacuum to give 461 mg fac-Ir(PMe$_3$)$_3$(BPin)$_3$ in quantitative yield. The product was recrystallized from concentrated pentane solution at −30° C. to give colorless crystal. $^1$H NMR (C$_6$H$_6$) δ 1.34 (s, 36H, BO$_2$C$_6$H$_{12}$, 1.52 (m, 27H, PMe$_3$). $^{11}$B NMR (C$_6$H$_6$) δ 36.0. $^{31}$P{$^1$H} NMR (C$_6$H$^6$) δ −64.

EXAMPLE 5

This example shows the synthesis of mer-Ir(PMe$_3$)$_3$(BPin)(H)(Ph).

HBPin (55 mg, 0.43 mmol) diluted in 2 mL pentane was added into a vial which was charged with Ir(PMe$_3$)$_3$Ph (194 mg, 0.39 mmol). The reaction mixture was stirred at ambient temperature for 30 minutes and the solvent was removed away under vacuum to give 241 mg mer-Ir(PMe$_3$)$_3$(BPin)

(H)(Ph) in quantitative yield. The product was recrystallized from concentrated pentane solution at −30° C. to give colorless crystal.

$^1$H NMR (C$_6$D$_6$) δ −11.32 (dt, 131 Hz, 20 Hz, 1H, hydride), 1.16 (s, 12H, BO$_2$C$_6$H$_{12}$), 1.41 (m, 27H, PMe$_3$), 7.17–7.20 (m, 3H), 7.98 (b, 2H). $^{11}$B NMR (C$_6$D$_6$) δ 35.8. $^{31}$P{$^1$H} NMR (C$_6$D$_6$) δ −57.8 (t, 22.9 Hz, 1P), −45.6 (d, 22.0 Hz, 2P). Calc. C, (40.32); H, (7.25).

Found C, (39.95); H, (7.38).

EXAMPLE 6

This example shows the synthesis of fac-Ir(PMe$_3$)$_3$(BPin)(H)(Me).

HBPin (27 mg, 0.195 mmol) diluted in 2 mL pentane was added into a vial which was charged with Ir(PMe$_3$)$_4$Me (100 mg, 0.21 mmol). The reaction mixture was stirred at ambient temperature for 5 minutes and the solvent was removed under vacuum to give orange red color oily mixture of fac-Ir(PMe$_3$)$_3$(BPin)(H)(Me) (83%) and mer-Ir(PMe$_3$)$_3$(Me)(H)(BPin) (17%) 94 mg in 75% yield. fac-Ir(PMe$_3$)$_3$(BPin)(H)(Me). $^1$H NMR (C$_6$D$_6$) δ −11.30 (dt, 140.4 Hz, 18.9 Hz, 1H, hydride), 0.40 (m, 3H, Me), 1.25 (s, 12H, BO$_2$C$_6$H$_{12}$, 1.17 (d, 6.4 Hz, 9H, PMe$_3$), 1.35 (d, 7.3 Hz, 9H, PMe$_3$), 1.47 (d, 7.9 Hz, 9H, PMe$_3$). $^{11}$B NMR (C$_6$D$_6$) δ 38.6. $^{31}$P{$^1$H} NMR (C$_6$D$_6$) δ −63.3 (br, 1P, PMe$_3$ trans to BPin), −56.83 (dd, 13.4 Hz, 23.2 Hz, 1P, PMe$_3$), −55.16 (dd, 13.4 Hz, 18.3 Hz, 1P, PMe$_3$). mer-Ir(PMe$_3$)$_3$(Me)(H)(BPin). $^1$H NMR (C$_6$D$_6$) δ −11.98 (dt, 131.9 Hz, 23.0 Hz, 1H, hydride), −0.06 (m, 3H, Me), 1.19 (s, 12H, BO$_2$C$_6$H$_{12}$, 1.14 (d, 29.9 Hz, 9H, PMe$_3$ trans to hydride), 1.54 (t, 3.4 Hz, 18H, 2 PMe$_3$ trans to each other). $^{11}$B NMR (C$_6$D$_6$) δ 38.6. $^{31}$P{$^1$H} NMR (C$_6$D$_6$) δ −57.8 (t, 1P, PMe$_3$ trans to hydride), −48.2 (d, 22.9 Hz, 2P, PMe$_3$ trans to each other).

EXAMPLE 7

This example shows the synthesis of (η$^5$-C$_5$Me)Rh(PMe$_3$)(H)(BPin).

HBPin (486 mg, 3.8 mmol) diluted in 2 mL mesitylene was added into an air-free flask which was charged with Cp*Rh(PMe$_3$)(H)$_2$ (400 mg, 1.26 mmol) in 8 mL mesitylene. The reaction mixture was heated at 110° C. in an oil bath for 2.5 days. The solvent was removed under vacuum to give 480 mg Cp*Rh(PMe$_3$)(H)(BPin) as brown oil in 87% yield. $^1$H NMR (C$_6$D$_6$) δ −13.94 (vt, 35.2 Hz, 1H, hydride), 1.15 (s, 12H, BO$_2$C$_6$H$_{12}$), 1.28 (dd, 9.8 Hz, 1.4 Hz, 9H, PMe$_3$), 2.07 (m, 15H, Cp*). $^{11}$B NMR (C$_6$D$_6$) 842.8. $^{31}$P{$^1$H} NMR (C$_6$D$_6$) δ 6.3 (t, 166.3 Hz, 1P, PMe$_3$).

EXAMPLE 8

This example shows the synthesis of Ir(PMe$_3$)$_4$(BPin).

PMe$_3$ (161 mg, 2.1 mmol) diluted in 4 mL THF was added into the schlenk tube which was charged with mer,cis-Ir(PMe$_3$)$_3$(BPin)$_2$Cl (500 mg, 0.7 mmol) in 5 mL THF. KOBu$^t$ (158 mg, 1.4 mmol) dissolved in 5 mL THF was then added to the reaction mixture. The reaction mixture was stirred at room temperature for 90 minutes. The solvent was removed under vacuum. The product was extracted into 8 mL pentane, followed by concentrating filtrate to give 402 mg of Ir(PMe$_3$)$_4$(BPin) in 92% yield. The product was recrystallized from concentrated pentane solution at −30° C. to give colorless crystal. $^1$H NMR (C$_6$D$_6$) 81.24 (s, 12H, BO$_2$C$_6$H$_{12}$), 1.58 (b, 36H, PMe$_3$). $^{11}$B NMR (C$_6$D$_6$) δ 38. $^{31}$P{$^1$H} NMR (C$_6$D$_6$) δ −57.5. Calc. C, (34.67); H, (7.76). Found C, (34.76); H, (7.89).

EXAMPLE 9

This example shows the synthesis of precatalyst 11 in a NMR reaction.

Ir(PMe$_3$)$_4$H (15 mg, 0.03 mmol) was dissolved in C$_6$D$_6$ (332 μL) in a GC vial and transferred to a J. Young NMR tube. Additional C$_6$D$_6$ (166 μL) was used to wash the residue into the NMR tube. HBPin (4.4 μL, 0.03 mmol) was added into the NMR tube directly via microsyringe. At room temperature, the starting material was gradually converted into the mixture of mer,cis-Ir(PMe$_3$)$_3$(H)$_2$(BPin) and fac-Ir(pMe$_3$)$_3$(H)$_2$(BPin). The sample was allowed to stand at room temperature for 6 days, and mer,cis-Ir(PMe$_3$)$_3$(H)$_2$(BPin) was gradually isomerized to give fac-Ir(PMe$_3$)$_3$(H)$_2$(BPin) as the major species. mer,cis-Ir(PMe$_3$)$_3$(H)$_2$(BPin). $^1$H NMR (C$_6$D$_6$) δ −12.18 (dt, J=114.7, 23.2 Hz, 1H, hydride trans to PMe$_3$), −10.46 (q, 1H, hydride trans to BPin), 1.21 (s, 12H, BO$_2$C$_6$H$_{12}$), 1.49 (d, 9H, PMe$_3$ trans to hydride), 1.69 (t, 3.5 Hz, 18H, 2 PMe$_3$ trans to each other). $^{11}$B NMR (C$_6$D$_6$) δ 38.6. $^{31}$P{$^1$H} NMR (C$_6$D$_6$) δ −58.1 (t, 22.6 Hz, 1P), −48.1 (d, 22.6 Hz, 2P). fac-Ir(PMe$_3$)$_3$(H)$_2$(BPin). $^1$H NMR (C$_6$D$_6$) δ −11.83 (symmetrical second order m, 2H, hydride), 1.25 (s, 12H, BO$_2$C$_6$H$_{12}$), 1.32 (d, 7.0 Hz, 9H, PMe$_3$ trans to BPin), 1.69 (d, 7.6 Hz, 18H, 2 PMe$_3$ trans to hydride). $^{11}$B NMR (C$_6$D$_6$) δ 38.6. $^{31}$P{$^1$H} NMR (C$_6$D$_6$) δ −62.0 (br, 1P, PMe$_3$ trans to BPin), −54.59 (d, 23.2 Hz, 2P, PMe$_3$ trans to hydride).

EXAMPLE 10

This example shows the generation of mer,trans-Ir(PMe$_3$)$_3$ (BPin)$_2$(H) and fac-Ir(PMe$_3$)$_3$(BPin)$_2$(H) in a benzene-d$_6$ solution.

B$_2$Pin$_2$ (7.9 mg, 0.031 mmol) dissolved in C$_6$D$_6$ (166 μL) was transferred to a J. Young NMR tube which was charged with Ir(PMe$_3$)$_4$H (15.4 mg, 0.031 mmol) in C$_6$D$_6$ (166 μL). Additional C$_6$D$_6$ (332 μL) was used to wash the residue into the NMR tube. The reaction mixture was then heated up at 60° C. The reaction was monitored by $^1$H, $^{11}$B, $^{31}$P NMR spectra. The starting materials were gradually converted into the mixture of mer,trans-Ir(PMe$_3$)$_3$(BPin)$_2$(H) and fac-Ir(PMe$_3$)$_3$(BPin)$_2$(H). fac-Ir(PMe$_3$)$_3$(BPin)$_2$(H) was the major species after the temperature was taken up to 100° C. for 7 hours. mer,trans-Ir(PMe$_3$)$_3$(BPin)$_2$(H). $^1$H NMR (C$_6$D$_6$) δ −12.36 (dt, J=117 Hz, 21.7 Hz, 1H, hydride trans to PMe$_3$), 1.22 (s, 12H, BO$_2$C$_6$H$_{12}$), 1.49 (d, 8.0 Hz, 9H, PMe$_3$ trans to hydride), 1.74 (t, 3.4 Hz, 18H, 2 PMe$_3$ trans to each other). $^{11}$B NMR (C$_6$D$_6$) δ 38.9. $^{31}$P{$^1$H} NMR (C$_6$D$_6$) δ −59.6 (t, 22.0 Hz, 1P), −50.8 (d, 22.0 Hz, 2P). fac-Ir(PMe$_3$)$_3$(BPin)$_2$(H). $^1$H NMR (C$_6$D$_6$) δ −11.66 (dt, 118.1 Hz, 18.1 Hz, H, hydride trans to PMe$_3$), 1.29 (s, 24H, BO$_2$C$_6$H$_{12}$), 1.41 (vt, 18H, 2 PMe$_3$ trans to BPin), 1.58 (d, 8.0 Hz, 9H, PMe$_3$ trans to hydride). $^{11}$B NMR (C$_6$D$_6$) δ 38.6. $^{31}$P{$^1$H} NMR (C$_6$D$_6$) δ −61.8 (br, 2P, PMe$_3$ trans to BPin), −56.6 (t, 22.0 Hz, 1P, PMe$_3$ trans to hydride).

EXAMPLE 11

This example shows the generation of Ir(PMe$_3$)$_2$(dppe)(BPin) in benzene-d$_6$.

dppe (8 mg, 0.02 mmol) dissolved in C$_6$D$_6$ (166 μL) was transferred to a J. Young NMR tube which was charged with Ir(PMe$_3$)$_4$(BPin) (12.5 mg, 0.02 mmol) in C$_6$D$_6$ (166 μL). Additional C$_6$D$_6$ (166 μL) was used to wash the residue into the NMR tube. The reaction mixture was allowed to stand at room temperature for 3 days to give Ir(PMe$_3$)$_2$(dppe)(BPin) as the major metal complex. $^1$H NMR (C$_6$D$_6$) δ 1.10 (s, 12H, BO$_2$C$_6$H$_{12}$), 1.33 (t, 3.3 Hz, 18H, 2 PMe$_3$), 1.92–2.18 (m, 4H, CH$_2$), 6.98–7.12, 7.16–7.28, 7.72–7.89, 7.91–7.98 (m, 20H, phenyl groups). $^{11}$B NMR (C$_6$D$_6$) δ 38.8. $^{31}$P{$^1$H} NMR (C$_6$D$_6$) δ −58.9 (dd, 141.6 Hz, 26.8 Hz, 2P, PMe$_3$), 39.1 (td, 141.6 Hz, 13.4 Hz, 1P, PPh$_2$ cis to BPin), 46.1 (br, 1P, PPh$_2$ trans to BPin).

EXAMPLE 12

This example shows the catalytic synthesis of 5-(4,4,5,5-Tetramethyl-1,3,2-dioxaborolyl)-1,3-bis(trifluoromethyl) benzene from 1,3-bis(trifluoromethyl)benzene and excess HBPin using precatalyst 8 and diphenylphosphinoethane (dppe).

Compound 8, (194 mg, 0.47 mmol) and dppe (186 mg, 0.47 mmol) were dissolved HBPin (4.5 g, 35 mmol). The solution was then added to a schlenk tube containing 1,3-bis(trifluoromethyl)benzene (5.0 g, 23.4 mmol). The reaction mixture was heated at 100° C. in an oil bath for 22 h. The brown solid obtained was sublimed at 80° C. (0.03 mrnHg) to yield 1,3,5-C$_6$H$_3$(CF$_3$)$_2$(BPin) as a colorless solid (6.21 g, 78% based on 1,3-bis(trifluoromethyl)benzene).

EXAMPLE 13

This example shows the catalytic synthesis of 5-(4,4,5,5-Tetramethyl-1,3,2-dioxaborolyl)-1,3-bis(trifluoromethyl) benzene from 1,3-bis(trifluoromethyl)benzene and excess HBPin using precatalyst [Ir(COD)Cl]$_2$ and diphenylphosphinoethane (dppe).

[Ir(COD)Cl]$_2$ (157 mg, 0.47 mmol) and dppe (186 mg, 0.47 mmol) were dissolved HBPin (4.5 g, 35 mmol). The solution was then added to a schlenk tube containing 1,3-bis(trifluoromethyl)benzene (5.0 g, 23.4 mmol). The reaction mixture was heated at 100° C. in an oil bath for 86 h. The brown solid obtained was sublimed at 80° C. (0.03 mmHg) to yield 1,3,5-C$_6$H$_3$(CF$_3$)$_2$(BPin) as a colorless solid (6.84 g, 86% based on 1,3-bis(trifluoromethyl)benzene).

EXAMPLE 14

This example shows the catalytic synthesis of (4,4,5,5-Tetramethyl-1,3,2-dioxaborolyl)benzene from benzene and HBPin using precatalyst 8 and dimethylphosphinoethane (dmpe).

Precatalyst 8 (6.5 mg, 0.016 mmol) and dmpe (0.12 M in benzene, 127 μL, 0.016 mmol) were dissolved in benzene (875 μL). After 30 min at room temperature, the precatalyst solution was transferred to an air-free flask to which HBPin (1.0 g, 7.8 mmol) and benzene (9 μL) were added. The reaction mixture was heated at 150° C. in an oil bath for 11 h. The pale brown solution was rotary evaporated to dryness. The brown viscous oil obtained was vacuum distilled to yield PhBPin as a colorless viscous oil (1.45 g, 91% at 66–67° C. (0.03 mmHg).

EXAMPLE 15

This example shows the catalytic synthesis of (4,4,5,5-tetramethyl-1,3,2-dioxaborolyl)benzene from benzene and HBPin using [Ir(COD)Cl]$_2$ and dimethylphosphinoethane (dmpe).

[Ir(COD)Cl]$_2$ (5.2 mg, 0.016 mmol) and dmpe (0.016 M in benzene, 258 μL, 0.016 mmol) were dissolved in benzene (740 μL). After 30 min at room temperature, the precatalyst solution was transferred to an air-free flask to which HBPin (1.0 g, 7.8 mmol) and benzene (9 μL) were added. The reaction mixture was heated at 150° C. in an oil bath for 6 h. The pale brown solution was rotary evaporated to dryness. The brown viscous oil obtained was vacuum distilled to yield PhBPin as a colorless viscous oil (1.49 g, 93%) at 66–67° C. (0.03 mmHg).

EXAMPLE 16

This example shows the catalytic synthesis of 1,3,5-C$_6$F$_3$-2,4,6-(BPin)$_3$ from 1,3,5-trifluorobenzene and excess HBPin using precatalyst 8 and dimethylphosphino-ethane (dmpe) in cyclohexane.

Precatalyst 8 (8.7 mg, 0.021 mmol), dmpe solution (0.13 M in cyclohexane, 158 μL, 0.021 mmol) and 1,3,5-trifluorobenzene (23 mg, 0.18 mmol) were dissolved in cyclohexane (440 μL) and transferred to a J. Young NMR tube. The reaction mixture was heated at 150° C. and monitored by $^{11}$B, $^{19}$F, and $^1$H NMR. $^{11}$B NMR (C$_6$D$_{12}$) δ 28.32 (d, $^1$J$_{BH}$=175.1 Hz, HBPin), 30.9 (sh, 1,3,5-C$_6$F$_3$-2, 4,6-(BPin)$_3$). $^{19}$F NMR (C$_6$D$_{12}$) δ −107.53 (s, 3F, 1,3,5-C$_6$H$_3$F$_3$), −105.20 (s, 1F, 1,3,5-C$_6$H$_2$F$_3$-2-BPin), −96.52 (s, 2F, 1,3,5-C$_6$H$_2$F$_3$-2-BPin), −94.00 (s, 2F, 1,3,5-C$_6$HF$_3$-2,4-(BPin)$_2$), −84.45 (s, 1F, 1,3,5-C$_6$HF$_3$-2,4-(BPin)$_2$), −81.91 (s, 3F, 1,3,5-C$_6$F$_3$-2,4,6-(BPin)$_3$]. After 17 h at 150° C., the reaction mixture was cooled to room temperature. 1,3,5-C$_6$H$_3$F$_3$-2,4,6-(BPin)$_3$ was precipitated as a colorless crystal (52 mg, 0.10 mmol). 1,3,5-C$_6$H$_3$F$_3$-2,4,6-(BPin)$_3$: $^1$H NMR (CDCl$_3$) δ 1.31 (s, 36H, BO$_2$C$_6$H$_{12}$). $^{13}$C NMR (CDCl$_3$) δ 24.70, 84.07, 173.10 (dt, $^1$J$_{CF}$=258.5 Hz, $^3$J$_{CF}$=17.1 Hz). $^{19}$F NMR (CDCl$_3$) δ −83.31. $^{11}$B NMR (CDCl$_3$) δ 29.1. MS (E.I.) m/z 510. Elemental analysis for C$_{24}$H$_{36}$B$_3$F$_3$O$_6$ calcd. C, (56.53%); H, (7.11%); N, (0.00%). Found C, (56.56%); H, (7.09%); N, (0.12%).

EXAMPLE 17

This example shows the catalytic synthesis of (4,4,5,5-tetramethyl-1,3,2-dioxaborolyl)benzene from benzene and HBPin using precatalyst 8 and diphenylphosphinoethane (dppe) in cyclohexane characterized by GC-FID.

Precatalyst 8 (2.9 mg, 7.0×10−3 mmol) and dppe (2.8 mg, 7.0×10$^{-3}$ mmol) in cyclohexane (0.5 mL) were transferred to a J. Young NMR tube. Decane (0.626 M in benzene, 50 μL, 0.0313 mmol decane and 0.47 mmol benzene) and HBPin (51 μL, 0.35 mmol) were added. The reaction mixture was heated at 100° C. and monitored by $^{11}$B NMR. $^{11}$B NMR (C$_6$D$_6$) δ 28.85 (d, $^1$J$_{BH}$=175.1 Hz, HBPin), 30.9 (br s, PhBPin). After for 67 h at 100° C., a small aliquot of the reaction mixture was diluted with CH$_2$Cl$_2$ and a GC-FID chromatogram was obtained. PhBPin (54% GC yield): GC-FID: 8.11 min (70° C., 2 min; 20° C./min; 250° C., 10 min). GC-MS: 7.71 min (70° C., 2 min; 20° C./min; 280° C., 10 min); (m/z) 204. $^1$H NMR (CDCl$_3$) δ 1.35 (s, 12H, BO$_2$C$_6$H$_{12}$), 7.34–7.39 (m, 2H), 7.43–7.49 (m, 1H), 7.81–7.84 (m, 2H).

EXAMPLE 18

This example shows the catalytic synthesis of (4,4,5,5-tetramethyl-1,3,2-dioxaborolyl)benzene from benzene and HBPin using precatalyst 8 and dimethylphosphinoethane (dmpe) to generate 12 in situ and characterized by GC-FID.

Precatalyst 8 (2.9 mg, 7.0×10$^{-3}$ mmol) was charged into a GC-vial in a glove box under N$_2$. Decane (0.626 M in benzene, 50 μL, 0.0313 mmol), HBPin (51 μL, 0.35 mmol), 1,2-bis(dimethylphosphino)ethane (0.0666 M in benzene, 105 μL, 7.0×10$^{-3}$ mmol) and benzene (345 μL) were added. The clear pale yellow solution was then transferred to a J. Young NMR tube. The reaction mixture was heated at 100° C. and monitored by $^{11}$B and 31P NMR. $^{11}$B NMR (C$_6$H$_6$) δ 28.85 (d, $^1$J$_{BH}$=175.1 Hz, HBPin), 30.9 (br s, PhBPin). $^{31}$P NMR ($C_6D_6$) δ −51.01 (unresolved t, 2P), −11.05 (unresolved d, 4P). After 31 h at 100° C., a small aliquot of the reaction mixture was diluted with $CH_2Cl_2$ and a GC-FID chromatogram was obtained. PhBPin (96% GC yield): GC-FID: 8.11 min (70° C., 2 min; 20° C./min; 250° C., 10 min). GC-MS: 7.71 min (70° C., 2 min; 20° C./min; 280° C., 10 min); (m/z) 204. $^1$H NMR (CDCl$_3$) δ 1.35 (s, 12H, $BO_2C_6H_{12}$), 7.34–7.39 (m, 2H), 7.43–7.49 (m, 1H), 7.81–7.84 (m, 2H).

EXAMPLE 19

This example shows the catalytic synthesis of (4,4,5,5-tetramethyl-1,3,2-dioxaborolyl)benzene from benzene and HBPin using precatalyst 9 and dimethylphosphinoethane (dmpe) to generate 12 in situ and characterized by GC-FID.

(MesH)Ir(BPin)$_3$ 9 solution (0.071 M in benzene, 100 μL, 7.0×10$^{-3}$ mmol), dmpe solution (0.070 M in benzene, 100 μL, 7.0×10$^{-3}$ mmol), decane solution (0.626 M. in benzene, 50 μL, 0.0313 mmol), HBPin (51 μL, 0.35 mmol) and benzene (250 μL) were mixed and transferred into a J. Young NMR tube was dissolved in $C_6D_6$ (400 μL) and dmpe solution (0.14 M in $C_6D_6$, 100 μL, 0.014 mmol) was added. The reaction mixture was transferred to a J. Young NMR tube. The reaction mixture was heated at 100° C. and monitored by $^{11}$B and $^{31}$P NMR. After for 177 h at 100° C., a small aliquot of the reaction mixture was diluted with $CH_2Cl_2$ and a GC-FID chromatogram was obtained. PhBPin (97% GC yield): GC-FID: 8.11 min (70° C., 2 min; 20° C./min; 250° C., 10 min). GC-MS: 7.71 min (70° C., 2 min; 20° C./min; 280° C., 10 min); (m/z) 204. $^1$H NMR (CDCl$_3$) 31.35 (s, 12H, $BO_2C_6H_{12}$), 7.34–7.39 (m, 2H), 7.43–7.49 (m, 1H), 7.81–7.84 (m, 2H).

EXAMPLE 20

This example shows the catalytic synthesis of $C_6H_4$(OMe)(BPin) as an isomeric mixture from anisole and HBPin using precatalyst 8 and trimethylphosphine characterized by GC-FID.

HBPin (45 mg, 0.35 mmol) was charged into a J. Young NMR tube. Precatalyst 8 (Indenyl)Ir(COD) (2.9 mg, 7.0×10$^{-3}$ mmol) in anisole (0.5 mL) was added. PMe$_3$ (1.5 μL, 0.014 mmol) was added via a microsyringe. The reaction mixture was then heated at 150° C. and monitored by $^{11}$B NMR. $^{11}$B NMR ($C_6H_6$) 328.66 (d, $^1J_{BH}$=175.1 Hz, HBPin), 31.2 [br s, $C_6H_4$(OMe)BPin]. After heating for 29 h at 150° C., a small aliquot of the reaction mixture was diluted with $CH_2Cl_2$ and a GC-FID chromatogram was obtained. The isomers, o-$C_6H_4$(OMe)(BPin):m-$C_6H_4$(OMe)(BPin):p-$C_6H_4$(OMe)(BPin) in a 9:74:17 ratio, were yielded (71 mg, 87%). GC-FID (70° C., 2 min; 20° C./min; 250° C., 10 min): 9.55 min (o-$C_6H_4$(OMe)(BPin)), 9.88 min (m-$C_6H_4$(OMe)(BPin)), 10.02 min (p-C6H4(OMe)(BPin)). GC-MS (70° C., 2 min; 20° C./min; 280° C., 10 min): 8.87 min, (m/z) 234 (o-$C_6H_4$(OMe)(BPin)); 9.14 min, (m/z) 234 (m-$C_6H_4$(OMe)(BPin)); 9.29 min, (m/z) 234 (p-$C_6H_4$(OMe)(BPin)).

EXAMPLE 21

This example shows the catalytic synthesis of 1,3,5-$C_6F_3$-2,4,6-(BPin)$_3$ from 1,3,5-trifluorobenzene and excess HBPin using precatalyst 8 and dimethylphosphino-ethane (dmpe) in neat.

Precatalyst 8 (29 mg, 0.07 mmol) and dmpe solution (10 mg, 0.07 mmol) were dissolved in HBPin (1.5 g, 11.7 mmol) and transferred to an air-free flask. 1,3,5-Trifluorobenzene (310 mg, 2.34 mmol) was added. The reaction mixture was heated at 150° C. for 62 h. After cooled to room temperature, the reaction mixture was washed with pentane (5×5 mL). It was decanted and dried over high vacuum overnight. A colorless crystal was collected (911 mg, 76%). 1,3,5-$C_6H_3F_3$-2,4,6-(BPin)$_3$: $^1$H NMR (CDCl$_3$) δ 1.31 (s, 36H, $BO_2C_6H_{12}$). $^{13}$C NMR (CDCl$_3$) δ 24.70, 84.07, 173.10 (dt, $^1J_{CF}$=258.5 HZ, $^3J_{CF}$=17.1 Hz). $^{19}$F NMR (CDCl$_3$) δ −83.31. $^{11}$B NMR (CDCl$_3$) δ 29.1. MS (E.I.) m/z 510.

Elemental analysis for $C_2H_{36}B_3F_3O_6$ calcd. C, (56.53%); H, (7.11%); N, (0.00%). Found C, (56.56%); H, (7.09%); N, (0.12%).

EXAMPLE 22

This example shows the catalytic synthesis of 1,3-C6B3CliBPin) as an isomeric mixture from 1,3-dichlorobenzene and excess HBPin using precatalyst 8 and diphenylphosphinoethane (dppe) in neat.

Precatalyst 8 (57 mg, 0.14 mmol) and dppe solution (54 mg, 0.14 mmol) were dissolved in HBPin (1.3 g, 10.2 mmol) and transferred to a schlenk tube. 1,3-Dichlorobenzene (1.0 mg, 6.8 mmol) was added. The reaction mixture was heated at 100° C. for 14 h. The product ratio of 1,3,5-$C_6H_3Cl_2$BPin to another unidentified mono-borylated product, determined by GC-FID of the crude reaction mixture, was 97:3. After removal of HBPin under high vacuum, the product was vacuum distilled at 93–94° C. (0.03 mmHg). A colorless viscous oil obtained. It was further purified by washing with 100 mL $H_2O$ (5×100 mL.) of the etherate solution of the product. After rotary evaporation and dried over high vacuum, a colorless oil obtained (1.65 g, 89%). 1,3,5-$C_6H_3Cl_2$BPin: GC-FID: 10.40 min. 1 (70° C., 2 min.; 20° C./min.; 250° C., 10 min.). GC-MS: 9.73 min. (70° C., 2 min.; 20° C./min.; 280° C., 10 min.); (m/z) 272. $^1$H NMR (CDCl$_3$) δ 1.32 (s, 12H, 13 $BO_2C_6H_{12}$), 7.41 (t, J=2.0 Hz, 1H), 7.63 (d, J=2.0 Hz, 2H). $^{13}$C NMR (CDCl$_3$) δ 24.82, 84.49, 131.06, 133.72, 134.72.

EXAMPLE 23

This example shows the catalytic synthesis of (4,4,5,5-tetramethyl-1,3,2-dioxaborolyl)benzene from benzene and HBPin using precatalyst 11 generated in situ and characterized by GC-FID.

Precatalyst 9 (4.9 mg, 7.0×10$^{-3}$ mmol) was charged into a GC-vial in a glove box under $N_2$. Decane (0.626 M in benzene, 50 μL, 0.0313 mmol), HBPin (51 μL, 0.35 mmol), 1,2-bis(di-tert-butylphosphino)ethane (2.2 mg, 7.0×10$^{-3}$ mmol) and benzene (450 μL) were added. The clear pale yellow solution was then transferred to a J. Young NMR tube. The reaction mixture was heated at 100° C. and monitored by $^{11}$B and $^{31}$P NMR. $^{11}$B NMR ($C_6H_6$ δ 28.85 (d, $^1J_{BH}$=175.1 Hz, HBPin), 30.9 (br s, PhBPin). $^{31}$P NMR ($C_6D_6$) δ −51.01 unresolved t, 2P), −11.05 (unresolved d, 4P). After for 31 h at 100° C., a small aliquot of the reaction mixture was diluted with $CH_2Cl_2$ and a GC-FID chromatogram was obtained. PhBPin (11% GC yield): GC-FID: 8.11 min. (70° C., 2 min.; 20° C./min.; 250° C., 10 min.). GC-MS: 7.71 min. (70° C., 2 min.; 20° C./min.; 280° C., 10 min.); (m/z) 204. $^1$H NMR (CDCl$_3$) O 1.35 (s, 12H, BO2C~1z), 7.34–7.39 (m, 2H), 7.43–7.49 (m, 1H), 7.81–7.84 (m, 2H).

EXAMPLE 24

This example shows the catalytic synthesis of IC$_6$H$_4$(BPin) as an isomeric mixture from iodobenzene and HBPin using precatalyst 9 and dppe.

HBPin (485 μL, 3.34 mmol) was charged into an air-free flask. Precatalyst Ir(MesH)(BPin)$_3$ 9 (46 mg, 0.067 mmol) and dppe (27 mg, 0.067 mmol) were dissolved in iodobenzene (6.7 g, 33 mmol) and transferred to the air-free flask. The reaction mixture was then heated at 100° C. and monitored by $^{11}$B NMR. $^{11}$B NMR (C$_6$H$_6$) δ 27.5 (d, $^1J_{BH}$=175.1 Hz, HBPin), 28.5 (br s, IC$_6$H$_4$(BPin)). After heating for 57 h at 100° C., the reaction was stopped. Iodobenzene was then vacuum distilled off at r.t. (0.03 mmHg). IC$_6$H$_4$(BPin) was vacuum distilled off at 93–95° C. (0.03 mmHg) as a colorless viscous liquid. It was further purified by washing with H$_2$O (3×25 mL) the etherate solution. The organic layer was rotary evaporated to dryness and vacuum dried. The isomers, m-C$_6$H$_4$I(BPin):p-C$_6$H$_4$I (BPin) in a 77:23 ratio, were yielded (852 mg, 77%). GC-MS (70° C., 2 min.; 20° C./min.; 280° C., 10 min.): 10.12 min., (m/z) 330 m-C$_6$H$_4$I(BPin) and p-C$_6$H$_4$I(BPin) isomeric mixture. m-C$_6$H$_4$I(BPin): $^1$H NMR (CDCl$_3$, 600 MHz) δ 1.32 (s, 12H, BO$_2$C$_6$H$_{12}$), 7.09 (unresolved dd, 1H), 7.72–7.74 (m, 1H), 7.75–7.77 (m, 1H), 8.12 (s, 1H). $^{13}$C NMR (CDCl$_3$, 125 MHz) δ 24.81, 84.05, 94.47, 129.58, 133,59, 140.02, 143.36. $^{11}$B NMR (CDCl$_3$) δ 30.2. p-C$_6$H$_4$I (BPin): $^1$H NMR (CDCl$_3$, 600 MHz) δ 1.31 (s, 12H, BO$_2$C$_6$H$_{12}$), 7.49 (d, J=7.9 Hz, 2H), 7.70 (d, J=7.9 Hz, 2H). $^{13}$C NMR (CDCl$_3$, 125 MHz) δ 24.81, 83.94, 98.77, 136.24, 136.85. $^{11}$B NMR (CDCl$_3$) δ 30.2.

EXAMPLE 25

This example shows the catalytic synthesis of 1,3,5-C$_6$H$_4$BrCl(BPin) from m-bromochlorobenzene and HBPin using precatalyst 8 and dppe.

m-Bromochlorobenzene (501 mg, 2.6 mmol) was charged into an air-free flask. Precatalyst (Indenyl)Ir(COD) 8 (22 mg, 0.052 mmol) and dppe (21 mg, 0.052 mmol) were dissolved in HBPin (570 μL g, 3.9 mmol) and transferred to the air-free flask. The reaction mixture was then heated at 100° C. and monitored by GC-FID. The reaction mixture was heated at 100° C. for 17 h. The product ratio of 1,3,5-C$_6$H$_3$ClBrBPin to another unidentified monoborylated product, determined by GC-FID of the crude reaction mixture, was 99:1. After removal of HBPin under high vacuum, the product was vacuum distilled at 98–99° C. (0.03 mmHg). A colorless viscous oil obtained (735 mg, 89%) which solidified as a colorless crystal. 1,3,5-C$_6$H$_3$ClBrBPin: GC-FID: 11.03 min. (70° C., 2 min.; 20° C./min.; 250° C., 10 min.). GC-MS: 10.22 min. (70° C., 2 min.; 20° C./min.; 280° C., 10 min.); (m/z) 318. $^1$H NMR (CDCl$_3$, 500 MHz) δ 1.32 (s, 12H, BO$_2$C$_6$H$_{12}$), 7.56 (unresolved dd, 1H), 7.67–7.68 (m, 1H), 7.78 (m, 1H). $^{13}$C NMR (CDCl$_3$) δ 24.82, 84.51, 122.63, 133.13, 133.82, 134.85, 135.56. $^{11}$B NMR (CDCl$_3$) δ 30.1.

EXAMPLE 26

This example shows the catalytic synthesis of Ph-BCat from benzene and HBCat using (Ind)Ir(COD).

(Ind)Ir(COD) (2.9 mg, 0.007 mmol) and dppe (2.8 mg, 0.007 mmol) were dissolved in C$_6$H$_6$ (166 μL) in a GC vial, and transferred to a J. Young NMR tube. HBCat (42 mg, 0.35 mmol) diluted in C$_6$H$_6$ (166 μL) was added into the NMR tube. Additional C$_6$H$_6$ (166 μL) was used to wash the residue into the NMR tube. The reaction mixture was heated at 150° C. in an oil bath. The conversion of the reaction was monitored by the disappearance of the resonance for HBCat in the $^{11}$B NMR spectra. The product was confirmed by GC-MS. GC-MS (m/z) 196.

EXAMPLE 27

This example shows the catalytic synthesis of Ph-BDAN from benzene and HBDAN using precatalyst (Ind)Ir(COD).

(Ind)Ir(COD) (2.9 mg, 0.007 mmol) and dppe (2.8 mg, 0.007 mmol) were dissolved in C$_6$H$_6$ (332 μL) in a GC vial, and transferred to the J. Young NMR tube which was charged with HBDAN (58.6 mg, 0.35 mmol). Additional C$_6$H$_6$ (166 μL) was used to wash down the residue into the NMR tube. The reaction mixture was heated at 150° C. in an oil bath. The conversion of the reaction was monitored by the disappearance of the resonance for HBDAN in the $^{11}$B NMR spectra. The product was confirmed by GC-MS. GC-MS (m/z) 244.

EXAMPLE 28

This example shows the catalytic synthesis of Ph-B(NH)$_2$C$_6$H$_4$ from benzene and HB(NH)$_2$C$_6$H$_4$ using precatalyst (Ind)Ir(COD).

Compound (Ind)Ir(COD) (2.9 mg, 0.007 mmol) and dppe (2.8 mg, 0.007 mmol) were dissolved in C$_6$H$_6$ (332 μL) in a GC vial, and transferred to the J. Young NMR tube which was charged with HB(NH)$_2$C$_6$H$_4$ (41.1 mg, 0.35 mmol). Additional C$_6$H$_6$ (166 μL) was used to wash down the residue into the NMR tube. The reaction mixture was heated at 150° C. in an oil bath. The conversion of the reaction was monitored by the disappearance of the resonance for HB(NH)$_2$C$_6$H$_4$ in the $^{11}$B NMR spectra. The product was confirmed by GC-MS. GC-MS (m/z) 194.

EXAMPLE 29

This example shows the catalytic synthesis of Ph-9-BBN from benzene and 9-BBN using precatalyst (Ind)Ir(COD).

(Ind)Ir(COD) (2.9 mg, 0.007 mmol) and dppe (2.8 mg, 0.007 mmol) were dissolved in C$_6$H$_6$ (332 μL) in a GC vial, and transferred to the J. Young NMR tube which was charged with 9-BBN (42.6 mg, 0.35 mmol). Additional C$_6$H$_6$ (166 μL) was used to wash down the residue into the NMR tube. The reaction mixture was heated at 150° C. in an oil bath. The conversion of the reaction was monitored by the appearance of the resonance for Ph-9-BBN in the $^{11}$B spectra. The product was further confirmed by comparing to authentic sample in GC-MS. GC-MS (m/z) 198.

EXAMPLE 30

This example demonstrates that benzotrifluoride is preferentially borylated in the presence of toluene by Ir(PMe$_3$)$_4$ (BPin).

Ir(PMe$_3$)$_4$(BPin), (15 mg, 0.024 mmol) was dissolved in a pre-mixed 1:1 (mole/mole) of benzotrifluoride and toluene (332 μL) in a GC vial, and transferred to a J. Young NMR tube. Additional solvent mixture (166 μL) was used to wash the residue into the NMR tube. The reaction mixture was heated at 150° C. in an oil bath. The conversion of the reaction was monitored by the disappearance of the resonance for Ir(PMe$_3$)$_4$(BPin) in the $^{11}$B and $^{31}$P NMR spectra. The isomer ratios were determined by the area ratio in the GC-FID chromatogram. The ratio of m-, p-C$_6$H$_4$(CF$_3$)(BPin): o-, m-, p-C$_6$H$_4$(Me)(BPin) is 88:12.

EXAMPLE 31

This example demonstrates that benzotrifluoride is preferentially borylated in the presence of toluene using a solution of (MesH)Ir(BPin)$_3$ and trimethylphosphine.

(MesH)Ir(BPin)$_3$, (5 mg, 0.007 mmol) was dissolved in a pre-mixed 1:1 (mole/mole) of benzotrifluoride and toluene (332 μL) in a GC vial. 1.5 μL PMe$_3$ was added to the mixture via a microsyringe. The mixture was transferred to a J. Young NMR tube. Additional solvent mixture (166 μL) was used to wash the residue into the NMR tube. Then HBPin (52 µL, 0.36 mmol) was added to the NMR tube via an autopipette. The reaction mixture was heated at 150° C. in an oil bath. The conversion of the reaction was monitored by the disappearance of the resonance for pinacolborane in the $^{11}$B NMR spectra. The isomer ratios were determined by the area ratio in the GC-FID chromatogram. The ratio of m-, p-$C_6H_4(CF_3)$(BPin): o-, m-, p-$C_6H_4$(Me)(BPin) is 94:6.

EXAMPLE 32

This example demonstrates that benzotrifluoride is preferentially borylated in the presence of toluene using a solution of (Ind)Ir(COD) and trimethylphosphine.

(Ind)Ir(COD) (3 mg, 0.007 mmol) was dissolved in a pre-mixed 1:1 (mole/mole) of benzotrifluoride and toluene (332 µL) in a GC vial. 1.5 µL PMe$_3$ was added to the mixture via a microsyringe. The mixture was transferred to a J. Young NMR tube. Additional solvent mixture (166 µL) was used to wash the residue into the NMR tube. Then HBPin (52 µL, 0.36 mmol) was added to the NMR tube via an autopipette. The reaction mixture was heated at 150° C. in an oil bath. The conversion of the reaction was monitored by the disappearance of the resonance for pinacolborane in the $^{11}$B NMR spectra. The isomer ratios were determined by the area ratio in the GC-FID chromatogram. The ratio of m-, p-$C_6H_4(CF_3)$(BPin): o-, m-, p-$C_6H_4$(Me)(BPin) is 94:6.

EXAMPLE 33

This example shows the catalytic synthesis of (4,4,5,5-tetramethyl-1,3,2-dioxaborolyl)benzene from benzene and HBPin using precatalyst 11 generated in situ and characterized by GC-FID.

Precatalyst 9 (4.9 mg, 7.0×10$^{-3}$ mmol) was charged into a GC-vial in a glove box under N$_2$. Decane (0.626 M in benzene, 50 µL, 0.0313 mmol), HBPin (51 µL, 0.35 mmol), 1,2-bis(di-tert-butylphosphino)ethane (2.2 mg, 7.0×10$^{-3}$ mmol) and benzene (450 µL) were added. The clear pale yellow solution was then transferred to a J. Young NMR tube. The reaction mixture was heated at 150° C. and monitored by $^{11}$B and $^{31}$P NMR. $^{11}$B NMR (C$_6$D$_6$) δ 28.85 (d, $^1J_{BH}$=175.1 Hz, HBPin), 30.9 (br s, PhBPin). $^{31}$P NMR (C$_6$D$_6$) δ -51.01 (unresolved t, 2P), -11.05 (unresolved d, 4P). After for 31 h at 100° C., a small aliquot of the reaction mixture was diluted with CH$_2$Cl$_2$ and a GC-FID chromatogram was obtained. PhBPin (74% GC yield): GC-FID: 8.11 min. (70° C., 2 min.; 20° C./min.; 250° C., 10 min.). GC-MS: 7.71 min. (70° C., 2 min.; 20° C./min.; 280° C., 10 min.); (m/z) 204. $^1$H NMR (CDCl$_3$) δ 1.35 (s, 12H, BO$_2$C$_6$H$_{12}$, 7.34–7.39 (m, 2H), 7.43–7.49 (m, 1H), 7.81–7.84 (m, 2H).

EXAMPLE 34

This example shows the catalysis by fac-Ir(PMe$_3$)$_3$(BPin)$_3$ in the presence of (MesH)Ir(BPin)$_3$.

(MesH)Ir(BPin)$_3$ (2.4 mg, 0.0035 mmol) and fac-Ir(PMe$_3$)$_3$(BPin)$_3$ (5.6 mg, 0.007 mmol) dissolved in C$_6$H$_6$ (300 µL) were transferred into the J. Young NMR tube which was charged with decane (0.632 M in benzene, 50 µL, 0.0316 mmol), and HBPin (51 µL, 0.35 mmol). Additional C$_6$H$_6$ (150 µL) was used to wash the residue into the NMR tube. The reaction mixture was heated at 150° C. in an oil bath. The conversion of the reaction was monitored by the disappearance of the resonance for pinacolborane in the $^{11}$B NMR spectra. After 16 hours at 150° C., a small aliquot of the reaction mixture was diluted with CH$_2$Cl$_2$ and a GC-FID chromatogram was obtained. PhBPin (91% GC yield).

EXAMPLE 35

This example shows the catalytic synthesis of (4,4,5,5-tetramethyl-1,3,2-dioxaborolyl)-benzene from benzene and HBPin using precatalyst 5.

Compound 4 (112 mg, 0.36 mmol) and HBPin (277 mg, 2.17 mmol) were dissolved in was dissolved in 5 ml of benzene. The solution was transferred to a thick-walled reaction vessel, which was heated for 84 h at 120° C. Compound 4 was converted to compound 5 well before the onset of catalysis. Residual solvent was removed from the reaction mixture and the residue was chromatographed on silica (CH$_2$Cl$_2$ eluant) to yield C$_6$H$_5$BPin as a colorless solid (153 mg, 0.760 mmol) in 34% yield based on HBPin.

EXAMPLE 36

This example shows the catalytic synthesis of 5-4,4,5,5-tetramethyl-1,3,2-dioxaborolyl)-1,3-bis(trifluoromethyl)benzene from 1,3-bis(trifluoromethyl)benzene and HBPin using precatalyst 7.

Compound 7, (5 mg, 0.013 mmol) and HBPin (90 mg, 0.70 mmol) were dissolved in 550 µL 1,3-bis(trifluoromethyl)benzene and heated at 150° C. in a constant temperature circulator for 3 hours in a J. Young NMR tube. The solution was transferred to a vial and the solvent removed under vacuum at room temperature. The residue was chromatographed on a silica gel column, eluting with CH$_2$Cl$_2$, to yield 1,3,5-C$_6$H$_3$(CF$_3$)$_2$(BPin) as a colorless solid (203 mg, 86% based on HBPin). C$_6$F$_5$(BPin). Catalytic addition of HBPin to C$_6$HF$_5$ using solutions of compounds 1 or 7 gave C$_6$F$_5$(BPin) as a colorless solid (205 mg, 81% based on HBPin, and 85 mg, 41% based on HBPin, for 1 and 3, respectively). mp 35–36° C. $^1$H NMR (CDCl$_3$) δ 1.36 (s, 12H, BO$_2$C$_6$H$_{12}$). $^{11}$B NMR (CDCl$_3$) δ 29. $^{19}$F NMR (CDCl$_3$) δ -129.5 (m, 2F), -149.7 (m, 1F), -161.9 (m, 2F). Calc. C. (49.02); H, (4.11). Found C, (48.33); H, (4.59). GC-MS (m/z) 294.

EXAMPLE 37

This example shows the catalytic synthesis of 5-(4,4,5,5-tetramethyl-1,3,2-dioxaborolyl)-1,3-dimethoxybenzene from 1,3-dimethoxybenzene and excess HBPin using precatalyst 7 in cyclohexane.

Compound 7 (5.0 mg, 0.012 mmol), 1,3-dimethoxybenzene (97 mg, 0.70 mmol) and HBPin (269 mg, 2.10 mmol) were dissolved in cyclohexane (1 mL) and transferred to an air-free flask. It was heated at 150° C. and monitored by GC-FID. GC-FID (70° C., 2 min; 20° C./min; 250° C., 10 min): 6.49 min (1,3-C$_6$H$_4$(OMe)$_2$), 11.19 min (1,3,4-C$_6$H$_3$(OMe)$_2$(BPin)), 11.35 min (1,3,5-C$_6$H$_3$(OMe)$_2$(BPin)). The product ratio of 1,3,5-C$_6$H$_3$(OMe)$_2$(BPin):1,3,4-C$_6$H$_3$(OMe)$_2$(BPin), determined by GC-FID of the crude reaction mixture, was 89:11. After heating for 32 h at 150° C. the solvent was removed under vacuum at room temperature, and the residue was chromatographed on silica gel (60–200 mesh) column, using hexanes to hexanes:ethyl acetate (9:1) as the gradient eluant. Solvent removal gave 1,3,5-C$_6$H$_3$(OMe)$_2$(BPin) as a white solid (114 mg, 62% based on 1,3-dimethoxybenzene). mp 88–90° C. Rf=0.40 (hexanes:ethyl acetate=9:1). $^1$H NMR (CDCl$_3$) δ 1.32 (s, 12H, BO$_2$C$_6$H$_{12}$), 3.79 (s, 6H, 2 OCH$_3$), 6.55 (t, J=2.4 Hz, 1H), 6.93 (d, J=2.4 Hz, 2H). $^{13}$C NMR (CDCl$_3$) δ 24.82, 55.40, 83.87, 104.50, 111.53, 160.35. $^{11}$B NMR (CDCl$_3$) δ 30.8. Elemental analysis for C$_{14}$H$_{21}$BO$_4$ calcd. C, (63.66%); H, (8.01%); N, (0.00%). Found C, (63.58%); H, (8.25%); N, (0.01%). GC-MS (m/z) 264.

EXAMPLE 38

This example shows the catalytic synthesis of (4,4,5,5-tetramethyl-1,3,2-dioxaborolyl)benzene from benzene and HBPin using precatalyst 7 in cyclohexane.

Compound 7 (5.0 mg, 0.012 mmol), benzene (109 mg, 1.4 mmol) and HBPin (45 mg, 0.35 mmol) were dissolved in cyclohexane (0.5 mL) and transferred to a J. Young NMR tube. The reaction was heated at 150° C. and monitored by $^{11}$B NMR. $^{11}$B NMR ($C_6H_{12}$) δ 28.65 (d, $^1J_{BH}$=175.1 Hz, HBPin), 31.3 (br s, PhBPin). After heating for 38 h at 150° C., the solvent was removed under high vacuum at room temperature, and the residue was chromatographed on silica gel using hexanes as the eluant. PhBPin (42 mg, 59% based on HBPin) was isolated as a colorless oil. Rf=0.17 (hexanes). $^1$H NMR (CDCl$_3$) O 1.35 (s, 12H, BO$_2$C$_6$H$_{12}$), 7.34–7.39 (m, 2H), 7.43–7.49 (m, 1H), 7.81–7.84 (m, 2H). GC-MS (m/z) 204.

EXAMPLE 39

This example shows the catalytic synthesis of a mixture of (4,4,5,5-tetramethyl-1,3,2-dioxaborolyl)benzene, 1,3-bis-(4,5,5-tetramethyl-1,3,2-dioxaborolyl)benzene, and 1,4-bis-(4,4,5,5-tetramethyl-1,3,2-dioxaborolyl)benzene from benzene and HBPin using precatalyst 7 in cyclohexane.

Compound 7 (5.9 mg, 0.014 mmol), benzene (60 mg, 0.77 mmol), and HBPin (90 mg, 0.70 mmol) were dissolved in cyclohexane (0.5 mL) and transferred to a J. Young NMR tube. The reaction was heated at 150° C. and monitored by $^{11}$B NMR. $^{11}$B NMR ($C_6H_{12}$) δ 28.65 (d, $^1J_{BH}$=175.1 Hz, HBPin), 31.7 (br s, PhBPin, 1,3-C$_6$H$_4$(BPin)$_2$ and 1,4-C$_6$H$_4$(BPin)$_2$). After heating for 87 h at 150° C., the solvent was removed under high vacuum at room temperature, and the residue was chromatographed on silica gel using hexanes as the eluant. PhBPin (59 mg, 41% based on HBPin) was isolated as a colorless oil. An isomer mixture of diborylated products C$_6$H$_4$(BPin)$_2$ was also isolated (39 mg, 33% based on HBPin). m-C$_6$H$_4$(BPin)$_2$:p-C$_6$H$_4$(BPin)$_2$=2:1 (determined by $^1$H NMR integrations). m-C$_6$H$_4$(BPin)$_2$: Rf=0.09 (hexanes). $^1$H NMR (CDCl$_3$) δ 1.32 (s, 24H, 2 BO$_2$C$_6$H$_{12}$), 7.36 (t, J=7.3 Hz, 1H), 7.88 (dd, J=7.3, 1.4 Hz, 2H), 8.26 (s, 1H). p-C$_6$H$_4$(BPin)$_2$: Rf=0.09 (hexanes). $^1$H NMR (CDCl$_3$) δ 1.33 (s, 24H, 2 BO$_2$C$_6$H$_{12}$, 7.79 (s, 4H).

EXAMPLE 40

This example shows the catalytic synthesis of 5-(4,4,5,5-tetramethyl-1,3,2-dioxaborolyl)-1,3-bis(trifluoromethyl)benzene from 1,3-bis(trifluoromethyl)benzene and HBPin using precatalyst 7 in cyclohexane.

Compound 7 (5.0 mg, 0.012 mmol), 1,3-bis(trifluoromethyl)benzene (75 mg, 0.35 mmol) and HBPin (45 mg, 0.35 mmol) were dissolved in cyclohexane (0.5 mL) and transferred to a J. Young NMR tube. The reaction mixture was heated at 150° C. and monitored by $^{11}$B NMR. $^{11}$B NMR ($C_6H_{12}$) δ 28.65 (d, $^1J_{BH}$=175.1 Hz, HBPin), 30.8 (brs, 1,3,5-C$_6$H$_3$(CF$_3$)$_2$(BPin)). After heating for 10 h at 150° C., the solvent was removed under high vacuum at room temperature, and the residue was chromatographed on silica gel using CH$_2$Cl$_2$ as the eluant. 1,3,5-C$_6$H$_3$(CF$_3$)$_2$(BPin) was isolated as a colorless solid (105 mg, 88%). $^1$H NMR (CDCl$_3$) 81.35 (s, 12H, BO$_2$C$_6$H$_{12}$, 7.93 (s, 1H), 8.22 (s, 1H). GC-MS (m/z) 340.

EXAMPLE 41

This example shows the catalytic synthesis of 1,3,5-C$_6$H$_4$Me$_2$(BPin) and 1,3-C$_6$H$_3$(CH$_3$)(CH$_2$BPin) as an isomeric mixture from m-xylene and HBPin using Compound 7 (10.0 mg, 0.025 mmol), m-xylene (75 mg, 0.70 mmol) and HBPin (90 mg, 0.70 mmol) were dissolved in cyclohexane (0.5 mL) and transferred to a J. Young NMR tube. The reaction mixture was heated at 150° C. and monitored by $^{11}$B NMR. $^{11}$B NMR ($C_6H_{12}$) δ 28.65 (d, $^1J_{BH}$=175.1 Hz, HBPin), 31.1 (br s, 1,3,5-C$_6$H$_3$(CH$_3$)$_2$(BPin) and 1,3-C$_6$H$_3$(CH$_3$)(CH$_2$BPin)). After heating for 59 h at 150° C., the solvent was removed under high vacuum at room temperature, and the residue was chromatographed on silica gel using hexanes as the eluant. The product ratio of 1,3,5-C$_6$H$_3$(CH$_3$)$_2$(BPin) and 1,3-C$_6$H$_3$(CH$_3$)(CH$_2$BPin), determined by GC-FID of the crude reaction mixture, was 94:6. 1,3,5-C$_6$H$_3$(CH$_3$)$_2$(BPin) and 1,3-C$_6$H$_3$(CH$_3$)(CH$_2$BPin) (91 mg, 56%) were isolated as a solid mixture of isomers. 1,3,5-C$_6$H$_3$(CH$_3$)$_2$(BPin): Rf=0.41 (hexanes). $^1$H NMR (CDCl$_3$) 81.33 (s, 12H, BO$_2$C$_6$H$_{12}$, 2.30 (s, 6H, 2 CH$_3$), 7.09 (s, 1H), 7.42 (s, 1H). GC-MS (m/z) 232.

EXAMPLE 42

This example shows the catalytic synthesis of 1,2,4-C$_6$H$_4$(OMe)$_2$(BPin) from veratrole and HBPin using precatalyst 7 in cyclohexane.

Compound 7 (5.0 mg, 0.025 mmol), veratrole (97 mg, 0.70 mmol) and HBPin (90 mg, 0.70 mmol) were dissolved in cyclohexane (0.5 mL) and transferred to a J. Young NMR tube. The reaction mixture was heated at 150° C. and monitored by $^{11}$B NMR. $^{11}$B NMR ($C_6H_{12}$) δ 28.65 (d, $^1J_{BH}$=175.1 Hz, HBPin), 31.4 (br s, 1,2,4-C$_6$H$_3$(OCH$_3$)$_2$ BPin)). The product ratio of uncharacterized 1,2-C$_6$H$_3$(OMe)$_2$(BPin):1,2,4-C$_6$H$_3$(OMe)$_2$(BPin), determined by GC-FID of the crude reaction mixture, was 98:2. After heating for 37 h at 150° C., the solvent was removed under high vacuum at room temperature, and the residue was chromatographed on silica gel using hexanes-ethyl acetate eluant gradient from 20:1 to 10:1. 1,2,4-C$_6$H$_3$(OCH$_3$)$_2$(BPin) was isolated as a colorless solid (118 mg, 64%). 1,2,4-C$_6$H$_3$(OCH$_3$)$_2$(BPin): mp 74–77° C. Rf=0.23 (hexanes:ethyl acetate=9:1). $^1$H NMR (CDCl$_3$) δ 1.32 (s, 12H, BO$_2$C$_6$H$_{12}$, 3.88 (s, 3H, OCH$_3$), 3.90 (s, 3H, OCH$_3$), 6.86 (d, J=8.0 Hz, 1H), 7.26 (d, J=1.5 Hz, 1H), 7.40 (dd, J=8.0, 1.5 Hz, 1H). $^{13}$C NMR (CDCl$_3$) δ 24.82, 55.71, 55.81, 83.63, 110.42, 116.46, 128.52, 148.28, 151.59. $^{11}$B NMR (CDCl$_3$) δ 30.3. Elemental analysis for C$_{14}$H$_{21}$BO$_4$ calcd. C, (63.66%); H, (8.01%); N, (0.00%). Found C, (63.41%); H, (8.18%); N, (0.01%). GC-MS (m/z) 264.

EXAMPLE 43

This example shows the catalytic synthesis of 1,2,4-C$_6$H$_4$(OMe)$_2$(BPin) from veratrole and excess HBPin using precatalyst 7 in cyclohexane.

Compound 7 (10.0 mg, 0.025 mmol), veratrole (97 mg, 0.70 mmol) and HBPin (270 mg, 2.1 mmol) were dissolved in cyclohexane (1 mL) and transferred to an air-free flask. The reaction mixture was heated at 150° C. and monitored by GC-FID. GC-FID (70° C., 2 min; 20° C./min; 250° C., 10 min): 6.19 min (1,2-C$_6$H$_4$(OMe)$_2$), 10.66 min (uncharacterized 1,2-C$_6$H$_3$(OMe)$_2$(BPin)), 11.27 min (1,2,4-C$_6$H$_3$(OMe)$_2$(BPin)). The product ratio of uncharacterized 1,2-C$_6$H$_3$(OMe)$_2$(BPin): 1,2,4-C$_6$H$_3$(OMe)$_2$(BPin), determined by GC-FID of the crude reaction mixture, was 99:1. After heating for 45 h at 150° C., the solvent was removed under high vacuum at room temperature, and the residue was chromatographed on silica gel using hexanes-ethyl acetate eluant gradient from 20:1 to 10:1. 1,2,4-C$_6$H$_3$(OCH$_3$)$_2$(BPin) was isolated as a colorless solid (153 mg, 82%).

EXAMPLE 44

This example shows the catalytic synthesis of 1,3,5-C$_6$H$_4$(OCH$_3$)(CH$_3$)(BPin) from 3-methylanisole and excess HBPin using precatalyst 7 in cyclohexane.

Compound 7 (15.0 mg, 0.037 mmol), 3-methylanisole (86 mg, 0.70 mmol) and HBPin (113 mg, 0.88 mmol) were dissolved in cyclohexane (1 mL) and transferred to an air-free flask. The reaction mixture was heated at 150° C. and monitored by GC-FID. GC-FID (70° C., 2 min; 20° C./min; 250° C., 10 min): 4.92 min (1,3-$C_6H_4$($OCH_3$)($CH_3$)), 10.23 min (uncharacterized 1,3-$C_6H_3$($OCH_3$)($CH_3$)(BPin)), 10.45 min (1,3,5-$C_6H_3$($OCH_3$)($CH_3$)(BPin)), 10.57 min (uncharacterized 1,3-$C_6H_3$($OCH_3$)($CH_3$)(BPin)). The product ratio of 1,3,5-$C_6H_3$($CH_3$)($OCH_3$)(BPin) to other unidentified mono-borylated products, determined by GC-FID of the crude reaction mixture, was 92:5:3. After heating for 25 h at 150° C., the solvent was removed under high vacuum at room temperature, and the residue was chromatographed on silica gel using hexanes to hexanes-ethyl acetate (20:1) as the gradient eluant. 1,3,5-$C_6H_3$($OCH_3$)($CH_3$)(BPin) (93 mg, 54%) was isolated as a colorless solid after chromatographed on silica gel using hexanes to hexanes:ethyl acetate (20:1) as the gradient eluant. 1,3,5-$C_6H_3$($OCH_3$)($CH_3$)(BPin): mp 55–56° C. Rf=0.52 (hexanes:ethyl acetate=20:1). $^1$H NMR (CDCl$_3$) δ 1.33 (s, 12H, BO$_2C_6H_{12}$), 2.31 (s, 3H, CH$_3$), 3.80 (s, 3H, OCH$_3$), 6.82 (m, 1H), 7.11 (d, J=2.5 Hz, 1H), 7.22 (m, 1H). $^{13}$C NMR (CDCl$_3$) δ 21.21, 24.83, 55.23, 83.76, 115.48, 118.79, 128.01, 138.91, 159.13. $^{11}$B NMR (CDCl$_3$) δ 30.9. Elemental analysis for $C_{14}H_{21}BO_3$ calcd. C, (67.77%); H, (8.53%); N, (0.00%). Found C, (67.54%); H, (8.53%); N, (0.02%). GC-MS (m/z) 248.

EXAMPLE 45

This example shows the catalytic synthesis of 1,3,5-$C_6H_4$($OCH_3$)($NMe_2$)(BPin) from m-N,N-dimethylanisidine and excess HBPin using precatalyst 7 in cyclohexane.

Compound 7 (10.0 mg, 0.025 mmol), m-N,N-dimethylanisidine (90 mg, 0.60 mmol) and HBPin (305 mg, 2.38 mmol) were dissolved in cyclohexane (1 mL) and transferred to an air-free flask. The reaction mixture was heated at 150° C. and monitored by GC-FID. GC-FID (70° C., 2 min; 20° C./min; 250° C., 10 min): 7.65 min (1,3-$C_6H_4$($OCH_3$)($NMe_2$)), 12.40 min (1,3,5-$C_6H_3$($OCH_3$)($NMez$)(BPin)), 12.60 min (uncharacterized 1,3-$C_6H_3$($OCH_3$)($NMe_2$)(BPin)). The product ratio of 1,3,5-$C_6H_3$($OCH_3$)($NMe_2$)(BPin) to another unidentified mono-borylated product, determined by GC-FID of the crude reaction mixture, was 95:5. After heating for 19 h at 150° C., the solvent was removed under high vacuum at room temperature, and the residue was sublimed (0.03 mmHg, 80° C.). 1,3,5-$C_6H_3$($OCH_3$)($NMez$)(BPin) was isolated as a colorless solid (124 mg, 75%). 1,3,5-$C_6H_3$($OCH_3$)($NMe_2$)(BPin): mp 64–66° C. Rf=0.33 (hexanes:ethyl acetate=9:1). $^1$H NMR (CDCl$_3$) δ 1.32 (s, 12H, BO$_2C_6H_{12}$), 2.93 (s, 6H, NMe$_2$), 3.81 (s, 3H, OCH$_3$), 6.37 (unresolved dd, 1H), 6.70 (d, J=2.2 Hz, 1H), 6.82 (d, J=2.5 Hz, 1H). $^{13}$C NMR (CDCl$_3$) δ 24.81, 40.72, 55.26, 83.65, 102.90, 106.22, 112.27, 151.59, 160.14. $^{11}$B NMR (CDCl$_3$) δ 30.8. Elemental analysis for $C_{15}H_{24}BNO_3$ calcd. C, (65.00%); H, (8.73%); N, (5.05%).

Found C, (65.25%); H, (8.98%); N, (4.86%). GC-MS (m/z) 277.

EXAMPLE 46

This example shows the catalytic synthesis of 1,3,5-$C_6H_4$($NMe_2$)$_2$(BPin) from m-N,N,N,N-tetramethylphenylenediamine and excess HBPin using precatalyst 7 in cyclohexane.

Compound 7 (15.0 mg, 0.037 mmol), m-N,N,N,N-tetramethylphenylenediamine (115 mg, 0.70 mmol) and HBPin (269 mg, 2.10 mmol) were dissolved in cyclohexane (1 mL) and transferred to an air-free flask. The reaction mixture was heated at 150° C. and monitored by GC-FID. GC-FID (70° C., 2 min; 20° C./min; 250° C., 10 min): 9.07 min (1,3-$C_6H_4$($NMe_2$)$_2$), 13.35 min (1,3,5-$C_6H_3$($NMe_2$)$_2$(BPin)), 13.53 min (uncharacterized 1,3-$C_6H_3$($NMe_2$)$_2$(BPin)). The product ratio of 1,3,5-$C_6H_3$($NMe_2$)$_2$(BPin) to another unidentified mono-borylated product, determined by GC-FID of the crude reaction mixture, was 97:3. After heating for 28 h at 150° C., the residue was filtered off and recrystallized from hot cyclohexane. 1,3,5-$C_6H_3$($NMe_2$)$_2$(BPin) was isolated as a colorless solid (140 mg, 69%). 1,3,5-$C_6H_3$($NMe_2$)$_2$(BPin): mp 178–180° C. Rf=0.22 (hexanes:ethyl acetate=5:1). $^1$H NMR (CDCl$_3$) δ 1.32 (s, 12H, BO$_2C_6H_{12}$), 2.94 (s, 12H, 2 NMe$_2$), 3.81 (s, 3H, OCH3), 6.23 (t, J=2.2 Hz, 1H), 6.65 (d, J=2.2 Hz, 2H). $^{13}$C NMR (CDCl$_3$) δ 24.81, 41.05, 83.43, 1.01.30, 108.77, 151.38. $^{11}$B NMR (CDCl$_3$) δ 31.0. HRMS for $C_{16}H_{27}BN_2O_2$ calcd. 290.2169, found 290.2167. GC-MS (m/z) 290.

EXAMPLE 47

This example shows the catalytic synthesis of N-$^i$Pr$_3$Si-pyrrole-3-BPin from N-$^i$Pr$_3$Si-pyrrole and excess HBPin using precatalyst 7 in cyclohexane.

Compound 7 (10.0 mg, 0.025 mmol), N-tri-iso-propylsilylpyrrole (156 mg, 0.70 mmol) and HBPin (269 mg, 2.10 mmol) were dissolved in cyclohexane (1 mL) and transferred to an air-free flask. The reaction mixture was heated at 150° C. and monitored by GC-FID. GC-FID (70° C., 2 min; 20° C./min; 250° C., 10 min): 8.85 min (N-$^i$Pr$_3$Si-pyrrole), 12.86 min (uncharacterized N-$^i$Pr$_3$Si-pyrrole-BPin), 13.05 min (N-$^i$Pr$_3$Si-pyrrole-3-BPin). The product ratio of N-$^i$Pr$_3$Si-pyrrole-3-BPin to another unidentified mono-borylated product, determined by GC-FID of the crude reaction mixture, was 99:1. After heating for 41 h at 150° C., the solvent was removed under high vacuum at room temperature, and the residue was chromatographed on silica gel using hexanes to hexanes:ethyl acetate (20:1) as the gradient eluant. N-$^i$Pr$_3$Si-pyrrole-3-BPin (199 mg, 81%) was isolated as a colorless oil. N-$^i$pr$_3$Si-pyrrole-3-BPin: Rf=0.43 (hexanes:ethyl acetate=20:1). $^1$H NMR (CDCl$_3$) δ 1.06 (d, J=7.3 Hz, 18H, 6 CH$_3$), 1.30 (s, 12H, BO$_2C_6H_{12}$), 1.44 (septet, J=7.3 Hz, 3H, 3 CH), 6.60 (dd, J=2.7, 1.2 Hz, 1H), 6.79 (dd, J=2.7, 2.0 Hz, 1H), 7.21–7.22 (unresolved dd, 1H). $^{13}$C NMR (CDCl$_3$) δ 11.62, 17.78, 24.84, 82.69, 115.57, 124.96, 133.65. $^{11}$B NMR (CDCl$_3$) δ 30.5. HRMS for $C_{16}H_{27}BN_2O_2$ calcd. 349.2612, found 349.2602. GC-MS (m/z) 290.

EXAMPLE 48

This example shows the catalytic synthesis of 1-trimethylsilyl-4,4,5,5-tetramethyl-1,3,2-dioxaborolane from N-trimethylsilylpyrrole and HBPin using precatalyst 7 and characterized by GC-MS.

Precatalyst 7 (5 mg, 0.012 mmol) and HBPin (45 mg, 0.35 mmol) were dissolved in N-trimethylsilylpyrrole (0.5 mL) and was transferred to a J. Young NMR tube in a glove box under N$_2$. The reaction mixture was heated at 150° C. and monitored by $^{11}$B NMR. $^{11}$B NMR (C$_6$H$_6$) δ 28.85 (d, $^1$J$_{BH}$=175.1 Hz, HBPin), 34.2 (br s, TMSBPin). After for 8 h at 150° C., a small aliquot of the reaction mixture was diluted with CH$_2$Cl$_2$ and a GC-MS chromatogram was obtained. TMSBPin (90% GC yield). GC-MS: 5.00 min. (70° C., 2 min.; 20° C./min.; 280° C., 10 min.): (m/z) 201.

EXAMPLE 49

In this example a two-step, one-pot protocol for the synthesis of a biaryl from an arene, a borane, and a halogenated aromatic is demonstrated. An arylboronate ester is first generated using an Ir catalyst, and is then subsequently coupled to the halogenated aromatic using a palladium catalyst.

To a small Schlenk tube equipped with a stir bar, in a glove box, was added HBPin (224 mg, 1.75 mmol) to mixture of 1,3-bis(trifluoromethyl)benzene (250 mg, 1.17 mmol), Ir(COD)(Indenyl) (9.7 mg, 0.023 mmol), and dppe (9.3 mg, 0.23 mmol). The tube was sealed and heated at 100° C. for 6 h. The reaction solution was allowed to cool to room temperature and Pd(PPh$_3$)4 (27.0 mg, 0.234 mmol), iodobenzene (217 mg, 1.06 mmol), Ba(OH)$_2$.8H$_2$O (552 mg, 1.75 mmol), and toluene (10 mL) were added. The mixture was stirred at 90–95° C. for 16.5 h. The mixture was allowed to cool, additional Ba(OH)$_2$.8H$_2$O (200 mg, 0.634 mmol) was added, and the solution stirred for 2 h at 90–95° C. Solvent was removed by rotary evaporation and the crude material subjected to column chromatography eluting with hexanes. 3,5-Bis(Trifluoromethyl)biphenyl was obtained (46 mg, 15%) as a colorless oil. The assignment was verified by comparison to the GC retention time and $^1$H NMR data to an authentic sample prepared from 3,5-bis(trifluoromethyl)phenyl pinacolborane and iodobenzene. $^1$H NMR (CDCl$_3$, 300 MHz) δ 8.00 (s, 2H), 7.93 (s, 1H), 7.85–7.58 (m, 2H), 7.53–7.42 (m, 3H).

EXAMPLE 50

This example shows the catalytic synthesis of N-3-chloro-5-(4,4,5,5-tetramethyl-1,3,2-dioxaborolyl)phenyl-2,5-dimethylpyrrole and HBPin in cyclohexane using precatalyst 8 and dimethylphosphinoethane (dmpe).

N-3-Chlorophenyl-2,5-dimethylpyrrole (535 mg, 2.6 mmol) was charged into an air-free flask. (Indenyl)Ir(COD) 8 (21 mg, 0.05 mmol), dmpe (7.5 mg, 0.05 mmol) and HBPin (1.0 g, 7.8 mmol) in cyclohexane (5 mL) was added. The reaction mixture was then heated at 100° C. for 44 h. N-3-chloro-5-(4,4,5,5-tetramethyl-1,3,2-dioxaborolyl)phenyl-2,5-dimethylpyrrole (93% GC-yield): GC-MS: 12.04 min. (70° C., min.; 20° C. min$^{-1}$; 280° C., 10 min.); (m/z) 331. $^1$H NMR (CDCl$_3$) δ 1.32 (s, 12H, BO$_2$C$_6$H$_{12}$), 2.00 (s, 6H, CH$_3$), 5.85 (s, 2H, pyrrolic protons), 7.29 (unresolved dd, 1H), 7.49–7.50 (m, 1H), 7.77–7.78 (m, 1H). $^{11}$B NMR (CDCl$_3$) δ 30.5.

EXAMPLE 51

In this example a two-step, one-pot protocol for the synthesis of a biaryl from an arene, a borane, and a halogenated aromatic is demonstrated. An arylboronate ester is first generated using an Ir catalyst, and is then subsequently coupled to the halogenated aromatic using a palladium catalyst.

Biphenyl: Closed system: To a J. Young NMR tube, in a glove box, was added benzene (437 mg, 5.60 mmol), Ir(COD)(indenyl) (3.0 mg, 0.0070 mmol), dppe (2.8 mg, 0.0070 mmol), dodecane (internal standard, 11.5 mg, 0.0675 mmol), and HBPin (45 mg, 0.352 mmol). The tube was sealed, removed from the box, and stirred at 100° C. for 18 h. The tube was allowed to cool to room temperature and Pd(PPh$_3$)$_4$ (8.1 mg, 0.007 mmol), K$_3$PO$_4$ (112 mg, 0.528 mmol), PhI (72.7 mg, 0.356 mmol), and DME (2 mL) were added. A GC-trace of the reaction mixture revealed PhBPin in 85.7% yield. Three freeze-pump-thaw cycles were performed to remove residual O$_2$ and the reaction mixture was heated at 80° C. for 2 days. GC analysis showed biphenyl (81.8% GC-yield), iodobenzene (7.9.7% GC-conversion), and PhBPin (79.1% GC-conversion).

EXAMPLE 52

In this example a two-step, one-pot protocol for the synthesis of a biaryl from an arene, a borane, and a halogenated aromatic is demonstrated. An arylboronate ester is first generated using an Ir catalyst, and is then subsequently coupled to the halogenated aromatic using a palladium catalyst.

Open system: To a Schenk tube, in a glove box, was added benzene (1.0 mL, 11.2 mmol), Ir(COD)(indenyl) (3.0 mg, 0.0070 mmol), dppe (2.8 mg, 0.0070 mmol), dodecane (internal standard, 12.0 mg, 0.070 mmol), and HBPin (45 mg, 0.352 mmol). The tube was sealed, removed from the box, and stirred at 100° C. for 18 h. The tube was allowed to cool to room temperature and Pd(PPh$_3$)$_4$ (8.5 mg, 0.0074 mmol), K$_3$PO$_4$ (112 mg, 0.528 mmol), PhI (74.9 mg, 0.367 mmol), and DME (2 mL) was added. A GC-trace of the reaction mixture revealed PhBPin in 78.9% yield. The reaction mixture was degassed by purging with N$_2$ and heated at 80° C. for overnight. GC analysis showed biphenyl (97.3% GC-yield), iodobenzene (84.1% GC-conversion), and PhBPin (90.7% GC-conversion).

EXAMPLE 53

A comparison of precatalysts Cp*(PMe$_3$)IR(H)(BPin) (2) and Cp*Rh(η$^4$-C$_6$Me$_6$) (7) in borylations of various substituted arenes revealed that the Ir system was more selective towards arene C—H activation (Cho et al., J. Am. Chem. Soc. 122: 12868–12869 (2000)). Given the importance of selectivity in chemical synthesis, these findings spurred a detailed investigation of the original Ir system. Those results are described herewith.

Compound 2 is stable in benzene solutions after prolonged thermolysis, which eliminates several mechanistic possibilities, including PMe$_3$ dissociation to generate Cp*Ir(H)(BPin), an analog of proposed intermediates in the Rh system. However, added PMe$_3$ strongly inhibits catalysis where HBPin is present. This indicated that small quantities of phosphine-Ir$^V$ species could be active. Since Cp*IrH$_{4-x}$(BPin)$_x$ species (x=1, 2) form in the thermolysis of Cp*IrH$_4$ and HBPin (Kawamura and Hartwig, J. Am. Chem. Soc. 123: 8422–8423 (2001)), anisole borylations with identical loadings of Cp*IrH$_4$ and 2 were compared. From this experiment, Cp*IrH$_{4-x}$(BPin)$_x$ intermediates can be eliminated because they are not kinetically competent for catalysis and the borylation regioselectivities for Cp*IrH$_4$ and 2 differ substantially. At 150° C., the following isomer ratios were obtained for anisole borylation with 20 mol % precatalyst loadings: Cp*IrH$_4$, o:m:p=3:49:48; 2 o:m:p=2:79:19.

Exclusion of a simple phosphine dissociative pathway narrows the plausible catalysts to two choices: (i) Ir phosphine species arising from Cp* loss or (ii) species where both Cp* and PMe$_3$ have been lost. The latter possibility was intriguing in light of Marder's synthesis of (η$^6$-arene)Ir(BCat)$_3$ complexes (Cat=ortho-catecholate) from (Ind)Ir(COD) (8, Ind η$^5$-C$_9$H$_7$, COD=1,5-cyclooctadiene) and HBCat in arene solvents. Using an analogous route, we prepared (η$^6$-mesitylene)Ir(BPin)$_3$ (9 wherein B(OR)$^2$ is BPin) in 19% yield from (Ind)Ir(COD) and HBPin (Compound 9 has been prepared as an analytically pure white solid. Relevant spectroscopic data included $^1$H NMR (C$_6$D$_6$) δ 1.33 (s, 36H, BO$_2$C$_6$H$_{12}$), 2.23 (s, 9H, C$_6$H$_3$(CH$_3$)$_3$), 5.62 (s, 3H, C$_6$H$_3$(CH$_3$)$_3$). $^{11}$B NMR (C$_6$D$_6$)

δ 32.5. $^{13}$C NMR (C$_6$D$_6$) δ 19.68, 25.73, 80.95, 96,97, 118.05). Compound 9 reacted with benzene at 150° C. to produce Ir metal and three equivalents of C$_6$H$_5$BPin, but did not catalyze C$_6$H$_5$BPin formation from benzene and HBPin. Thus, it appears that phosphines or related donor ligands are required for catalysis.

Utilizing the lability of the mesitylene ligand in 9, Ir phosphine species were generated in situ from 9 and appropriate phosphines and subsequently screened for activity. Borylation using 2 mol % 9 and 4 mol % PMe$_3$ was viable (Table 2, entry 1), and both catalytic activity and TONs for benzene borylation increased dramatically relative to precatalyst 2. Borylation rates were appreciable when [P]:[Ir] <3:1, but decreased dramatically when [P]:[Ir] ratio equals or exceeds 3:1.

The low isolated yields of 9 hampered screening efforts and precluded practical applications despite the dramatic improvement in catalytic activity. Hence, we sought alternative means for generating active catalysts. Since NMR spectra indicated quantitative generation of 9 from 8, in situ generation of active catalysts by phosphine addition to 8 was examined. Compound 8 was synthesized in 86% yield from indenyl lithium and [IrCl(COD)]$_2$ (Merola and Kacmarcik, Organometallics 8: 778–784 (1989)). This approach was successful and results for benzene borylations are shown in Table 2 (entries 2–5). Chelating phosphines substantially increased activity and TONs as highlighted for 1,2-bis (dimethylphosphino)ethane (dmpe) where the effective TON of 4500 (Table 2, entry 5) represented an improvement of more than 1000-fold over precatalyst 2.

TABLE 2[a]

| Ent. | Sub. | Arene:HBPin | Prod. | Cat. | Ligand | Temp (° C.) | Time (h) | Yield % |
|---|---|---|---|---|---|---|---|---|
| 1 | C$_6$H$_6$ | 16:1 | PhBPin | (MesH)Ir(BPin)$_3$ (9) | PMe$_3$ | 150 | 15 | 98[b] |
| 2 | C$_6$H$_6$ | 16:1 | PhBPin | (Ind)Ir(COD) (8) | PMe$_3$ | 150 | 18 | 88[b] |
| 3 | C$_6$H$_6$ | 16:1 | PhBPin | 8 | dppe | 150 | 2 | 95[b] |
| 4 | C$_6$H$_6$ | 16:1 | PhBPin | 8 | dmpe | 150 | 2 | 84 |
| 5 | C$_6$H$_6$ | 16:1 | PhBPin | 0.02 mol % 8 | dmpe | 150 | 61 | 90[b] |
| 6 | C$_6$H$_6$ | 16:1 | PhBPin | (IrCl(COD))$_2$ | dmpe | 150 | 8 | 74[b] |
| 7 | 1,3,5-trifluorobenzene | 4:1 | 2,4,6-trifluorophenyl-BPin | 8 | dmpe | 150 | 1 | 63 |
| 8 | 1,3,5-trifluorobenzene | 1:5 | tris-BPin trifluorobenzene | 8 | dmpe | 150 | 62 | 76 |
| 9 | 1,4-difluorobenzene | 4:1 | 2,5-difluorophenyl-BPin | 8 | dppe | 100 | 3 | 81 |
| 10 | 1,3-dichlorobenzene | 1:1.5 | 3,5-dichlorophenyl-BPin | 8 | dppe | 100 | 14 | 89 |
| 11 | 1,3-dibromobenzene | 1:1.5 | 3,5-dibromophenyl-BPin | 8 | dppe | 100 | 17 | 92 |

TABLE 2[a]-continued

| Ent. | Sub. | Arene:HBPin | Prod. | Cat. | Ligand | Temp (°C.) | Time (h) | Yield % |
|---|---|---|---|---|---|---|---|---|
| 12[c] | 2,6-dichloropyridine | 1:2 | 4-BPin-2,6-dichloropyridine | 8 | dppe | 100 | 4 | 69 |
| 13 | iodobenzene | 10:1 | — | 8 | dppe | 100 | 60 | — |
| 14 | iodobenzene | 10:1 | PinB-C6H4-I (m:p = 79:21) | 9 | dppe | 100 | 57 | 77 |
| 15[c] | methyl 3-chlorobenzoate | 1:2 | methyl 3-chloro-5-BPin-benzoate | 8 | dppe | 100 | 25 | 95 |
| 16 | 1,2-dimethoxybenzene | 1:3 | 4-BPin-1,2-dimethoxybenzene | 8 | dmpe | 150 | 95 | 82 |

[a]Reactions run in neat arene, Ir = 2 mol %, P:Ir = 2:1, and yields are reported for isolated materials unless otherwise noted. (COD = 1,5,-cyclooctadiene, dmpe = Me$_2$PCH$_2$CH$_2$PMe$_2$, dppe = Ph$_2$PCH$_2$CH$_2$PPh$_2$).
[b]GC yield based on HBPin.
[c]Reactions run in cyclohexane.

In addition, active catalysts were generated from commercially available sources such as [IrCl(COD)]$_2$ (Table 2, entry 6).

If the primary active species generated by PMe$_3$ addition to 8 and 9 are identical to those generated from 2, borylations of substituted benzenes should exhibit similar regio- and chemoselectivities. Anisole is a useful substrate for probing regioselectivity and the meta:para ratios determined from borylations by active species generated by PMe$_3$ addition to 8 and 9 are similar to those for 2 (For catalysts generated from 4 mol % PMe$_3$ and 2 mol % 8 or 9, the following isomer ratios were obtained for anisole borylation at 150° C.: 8, o:m:p=9:74:17; 9, o:m:p=8:75:17. For 8 and 9, ortho borylation increases slightly, which could signify a minor pathway that is not accessible from 2).

To assess chemoselectivities, the ratios of arene to benzylic activation in m-xylene were examined. The selectivities of catalysts generated from 8 (13:1) and 9 (12:1) were diminished relative to the selectivity of precatalyst 2 (35:1). Nevertheless, the Ir catalysts were more selective for arene activation than the Rh catalyst, 7, where the selectivity was 7:1 (Cho et al., J. Am. Chem. Soc. 122: 12868–12869 (2000)); a Rh catalyst that is highly selective for benzylic borylation has been recently reported (Shimada et al., Angew. Chem., Int. Ed. 40: 2168–2171 (2001)), and the addition of one equivalent of the chelating phosphine, 1,2-bis(diphenylphosphino)ethane (dppe) per equivalent of 8 or 9 generated catalysts where the arene to benzylic selectivities exceeded 142:1.

Dramatic differences in chemoselectivities between Ir and Rh catalysts were found for halogenated substrates, where the Ir catalysts preferentially activated C—H bonds. A representative procedure for borylation is given for entry 10 of Table 2. Briefly, in a glove box under N$_2$, compound 8 (57 mg, 0.14 mmol) and dppe (54 mg, 0.14 mmol) were dissolved in HBPin (1.30 g, 10.2 mmol). The solution was transferred to a thick-walled air-free flask containing 1,3-dichlorobenzene (1.00 g, 6.80 mmol). The clear yellow solution was heated at 100° C. under N$_2$ and monitored by GC-FID. After 14 hours, the reaction mixture was pumped down to obtain a brown oil, which was vacuum distilled at 93–94° C. (0.03 mmHg). The resulting oil was then dissolved in Et$_2$O (10 mL) and washed with water (5×100 mL). After drying over MgSO$_4$, ether was removed under high-vacuum to give 1.65 g (89% yield) of colorless 1,3,5-C$_6$H$_3$Cl$_2$BPin (mp 36–38° C.: $^1$H NMR (500 MHz. CDCl$_3$) δ 1.32 (s, 12H), 7.41 (t, J=2.0 Hz, 1H), 7.63 (d, J=2.0 Hz, 2H). $^{13}$C NMR (125 MHz, CDCl$_3$) δ 24.82, 84.49, 131.1, 133.7, 134.7. $^{11}$B NMR (CDCl$_3$) δ 30). Good yields of mono- or tri-borylated products of 1,3,5-trifluorobenzene were obtained by adjusting the arene:HBPin ratio (Table 2, entries 7 and 8). In contrast, previous attempts to effect multiple borylations of 1,3,5-trifluorobenzene using the Rh catalyst 7 led to increased defluorination (Cho et al., J. Am. Chem. Soc. 122: 12868–12869 (2000)). Borylations of aromatics with heavier halogen substituents provided an even starker contrast between Ir and Rh catalysts. For example, Ir catalyzed borylations of 1,3-dichlorobenzene and 1,3-dibromobenzene generate meta functionalized products in high yields (entries 10 and 11), while dehalogenation is the dominant pathway in Rh catalyzed reactions. Dechlorination was observed during attempted silylations of 1,3-dichlorobenzene using closely related Rh catalysts (Ezbiansky et al., Organometallics 17: 1455–1457 (1998). The finding that aromatic C-halogen bonds survived in the Ir catalyzed reactions contrasted the Pd-catalyzed reactions of boranes and aryl bromides where the C—Br bonds were converted to C—B or C—H bonds (Murata, et al., J. Org. Chem. 65: 164–168 (2000)). Entry 12 of Table 2 illustrates an extension of meta selective borylation to a halogenated heterocycle.

Since aryl iodides have the weakest carbon-hydrogen bonds, they are most susceptible towards reductive cleavage by transition metals. Hence, it is not surprising that the Ir catalysts generated from 8 were ineffective in aromatic borylation of iodobenzene (Table 2, entry 13). However, iodobenzene and HBPin reacted smoothly to yield a mixture of $C_6H_4I(BPin)$ isomers when active catalysts were generated from the $Ir^{III}$ source, 9, and dppe (Table 2, entry 14). Thus, Ir catalysts are compatible with the entire range of aryl halides. Furthermore, functional group tolerance that was previously found in Rh catalyzed borylations extends to Ir catalyzed reactions (viz., ester compatibility in entry 15 of Table 2) and Ir selectively borylates symmetrical 1,2-substituted arenes at the 4-position (Table 2, entry 16).

From a mechanistic standpoint, catalytic cycles involving oxidative addition/reductive elimination from $Ir^{I/III}$ and/or $Ir^{III/V}$ intermediates are consistent with the results herein. Within this context, we considered $Ir^I$ and $Ir^{III}$ boryl intermediates to be the most likely C—H activating species in the $Ir^{I/III}$ and $Ir^{III/V}$ cycles, respectively. Hence, the $Ir^I$ and $Ir^{III}$ boryl complexes, $Ir(BPin)(PMe_3)_4$ and $fac$-$Ir(BPin)_3(PMe_3)_3$, were prepared in order to evaluate their stoichiometric reactions with arenes.

Compounds $Ir(BPin)(PMe_3)_4$ and $fac$-$Ir(BPin)_3(PMe_3)_3$ have been fully characterized as shown by the following spectroscopic data: $Ir(BPin)(PMe_3)_4$, $^1H$ NMR $(C_6D_6, 25°$ C.) δ 1.24 (s, 12H, $BO_2C_6H_{12}$), 1.58 (b, 36H, $PCCH_3)_3$). $^{11}B$ NMR $(C_6D_6)$ δ 38. $^{31}P\{^1H\}$ NMR $(C_6D_6)$ δ –57.5; fac-Ir $(BPin)_3(PMe_3)_3$, $^1H$ NMR $(C_6D_6)$ δ 1.34 (S, 36H, $BO_2C_6H_{12}$), 1.52 (m, 27H, $P(CH_3)_3$). $^{11}B$ NMR $(C_6D_6)$ δ 36.0. $^{31}P\{^1H\}$ NMR $(C_6D_6)$ δ –64. In reactions with arenes, compounds $Ir(BPin)(PMe_3)_4$ and $fac$-$Ir(BPin)_3(PMe_3)_3$ both reacted cleanly with benzene to produce PhBPin and the corresponding hydride complexes shown in Equations 2 and 3 (FIGS. 4A and 4B, respectively), which was consistent with the idea that $Ir^I$ or $Ir^{III}$ species can effect arene borylation; however, the arene products from stoichiometric reactions of $Ir(BPin)(PMe_3)_4$ and $fac$-$Ir(BPin)_3(PMe_3)_3$ with iodobenzene differed substantially. Specifically, compound $Ir(BPin)(PMe_3)_4$ reacted rapidly with iodobenzene at room temperature, but isomers of $C_6H_4I(BPin)$ were not detected, even after prolonged thermolysis. Conversely, thermolysis of $fac$-$Ir(BPin)_3(PMe_3)_3$ in iodobenzene produced m- and p-$C_6H_4I(BPin)$ in 54% yield, based on $Ir(BPin)_3(PMe_3)_3$, in addition to a 45% yield of PhBPin.

Since conversion rates in catalytic reactions plummet when [P]:[Ir] ratios equal or exceed 3:1, the observation that $Ir(BPin)(PMe_3)_4$ and $fac$-$Ir(BPin)_3(PMe_3)_3$ were not kinetically competent for catalysis was expected. However, this does not exclude the possibility that identical intermediates are generated in the stoichiometric and catalytic reactions. Instead, generation of appropriate intermediates under catalytic conditions could simply be more efficient. Nevertheless, the stoichiometric transformations lend credence to either $Ir^I$ or $Ir^{III}$ species mediating C—H activations under catalytic conditions. The reactions of $Ir(BPin)(PMe_3)_4$ and $fac$-$Ir(BPin)_3(PMe_3)_3$ with iodobenzene have greater mechanistic implications. For example, the absence of $C_6H_4I(BPin)$ products in thermolysis of $Ir(BPin)(PMe_3)_4$ mirrored the failed attempt to borylate iodobenzene using the $Ir^I$ precatalyst 8 (Table 2, entry 13). The reactivity of $Ir(BPin)_3(PMe_3)_3$ suggests that an $Ir^{III}$ intermediate may activate C—H bonds in the presence of C—I bonds, but the chemistry of $Ir(BPin)(PMe_3)_4$ is more important because it essentially excludes the participation of $Ir^I$ species in the successful borylation of iodobenzene using the $Ir^{III}$ precatalyst 9 (Table 2, entry 14).

In summary, an investigation of the original Ir catalytic system, whose promising selectivities could not be practically implemented due to extremely low effective TONs, has produced a family of efficient borylation catalysts with remarkable regio- and chemoselectivities. In addition to providing a direct route to aryl and heteroaryl boron compounds from boranes and arenes, the viability of a tandem catalytic cascade where the first step is an Ir catalyzed aromatic borylation has been demonstrated.

EXAMPLE 54

This example provides a protocol for performing Rh catalyzed aromatic borylations in cyclohexane. Borylation at the 5-position of several 1,3-substituted aromatic species ranging from electron-rich (1,3-$(NMe_2)_2C_6H_4$) to electron-deficient (1,3-$(CF_3)_2C_6H_4$) yields the corresponding aryl boronate esters. Veratrole was selectively borylated at the 4-position, thus extending regioselectivity to 1,2-substituted benzenes. Selective borylation at the 3-position of an N-protected pyrrole has also been demonstrated, providing a valuable reagent for cross-coupling reactions in a single step.

We have developed a simple protocol for preparing arylboronate esters in good to moderate yields where the aromatic substrate is the limiting reagent. In addition, we have expanded the scope of selective meta borylation of 1,3-substituted benzenes and have extended the borylation chemistry to protected pyrrole.

For this study, we used Hartwig's precatalyst, $Cp*Rh(\eta^4$-$C_6Me_6)$ (4) (Chen et al., Science 2000, 287, 1995–1997) whose reactivity we compared to Ir precatalysts that were utilized for the catalytic aromatic borylation of C—H bonds. Although the Ir precatalysts seem to be more selective, their effective turnover numbers were too low for practical applications. The preferential activation of the stronger aryl C—H bonds in the presence of weaker benzylic C—H bonds is significant, particularly in light of Marder and co-worker's recent report of selective benzylic borylation using the precatalyst trans-$Rh(Cl)(PiPr_3)_2(N_2)$ (Shimada et al., Angew. Chem., Int. Ed. 2001, 40, 2168–2171).

Since solutions of 4 do not readily borylate secondary or tertiary C—H positions, cyclohexane was an obvious choice for an inert solvent. Indeed, catalytic borylations in cyclohexane using 2 mol % of 4 with a modest excess of pinacolborane (HBPin) gave boronate esters in reasonable yields (Table 3). Reactions were performed in sealed vessels at 150° C. until $^{11}B$ NMR spectra indicated that most of the borane had been consumed. Crude mixtures were analyzed by GC-MS and the reported yields are for isolated products. In cases where isomers were produced, compounds were separated by chromatography, unless otherwise noted.

We have found that trace solvent impurities can inhibit catalytic borylations. With the exception of benzene, the substrates have been selected to test the generality of sterically directed borylation.

For benzene three sets of conditions were employed (Table 3, entries 1–3). In the first case, borylation was examined with equimolar quantities of benzene and HBPin.

TABLE 3

| Entry | Arene | HPBin:arene | Time | Product (yield) |
|---|---|---|---|---|
| 1 | $C_6H_6$ | 1:4 | 36 h | PhBPin (59) |
| 2[a] | $C_6H_6$ | 1:1 | 57 h | PhBPin (41) m-, p-$C_6H_4(BPin)_2$ (33, m:p = 2:1) |
| 3[b] | $C_6H_6$ | 4:1 | 61 h | m-$C_6H_4(BPin)_2$ p-$C_5H_4(BPin)_2$ 1,3,5-$C_6H_3(BPin)_2$ |
| 4 | 1,3-(F$_3$C)$_2$C$_6$H$_4$ | 1:1 | 10 h | 3,5-(F$_3$C)$_2$C$_6$H$_3$(BPin) (88) |
| 5 | 1,3-(Me$_2$N)$_2$C$_6$H$_4$ | 3:1 | 28 h | 3,5-(Me$_2$N)$_2$C$_6$H$_3$(BPin) (69) |
| 6[c] | 1,3-(MeO)$_2$C$_6$H$_4$ | 3:1 | 32 h | 3,5-(MeO)$_2$C$_6$H$_3$(BPin) (62) |
| 7 | 3-MeO-C$_6$H$_4$-NMe$_2$ | 4:1 | 19 h | 3-MeO-5-Me$_2$N-C$_6$H$_3$(BPin) (75) |
| 8[d] | m-xylene | 1:1 | 59 h | 3,5-Me$_2$C$_6$H$_3$(BPin) (53) |
| 9 | 3-MeO-C$_6$H$_4$-Me | 1.2:1 | 25 h | 3-MeO-5-Me-C$_6$H$_3$(BPin) (54) |
| 10 | 1,2-(MeO)$_2$C$_6$H$_4$ | 3:1 | 45 h | 1,2-(MeO)$_2$-4-BPin-C$_6$H$_3$ (82) |
| 11 | $^i$Pr$_3$Si-pyrrole | 3:1 | 41 h | 3-BPin-N($^i$Pr$_3$Si)-pyrrole (81) |

[a] Diborylated isomers were not separated;
[b] isomer mixture containing small amounts of PhBPin;
[c] 1,2,3-(OMe)$_2$C$_6$H$_3$(BPin) was isolated in 2% yield;
[d] m-C$_6$H$_4$(Me)(CH$_2$BPin) was isolated in 6% yield.

The isolated yields of products based on borane as the limiting reagent are 41% for PhBPin and 33% for $C_6H_4(BPin)_2$ both as a 2:1 mixture of meta and para isomers. Using a 4:1 ratio of benzene to borane, diborylation is minimized and PhBPin can be isolated in 59% yield. If a moderate excess of HBPin is used, the major species in the crude reaction mixture are m-$C_6H_4(BPin)_2$, p-$C_6H_4(BPin)_2$, and 1,3,5-$C_6H_3(BPin)_3$ in an approximate 1.0:1.2:1.7 ratio as determined from GC and NMR data. Further purification was not attempted; however, comparison of the weight of the crude mixture (311 mg) to the combined weights of HBPin, $C_6H_6$, and catalyst (340 mg) indicates efficient conversion to borylated species.

In cyclohexane solvent, 1,3-substituted arenes yield 1,3,5-substituted aryl boronate esters as major products (entries 4–9). Reactivities for arene substrates were similar except for 1,3-(CF$_3$)$_2$C$_6$H$_4$, which was substantially more reactive. In a previous report (Cho et al., J. Am. Chem. Soc. 2000, 122, 12868–12869), significant benzylic activation was observed in neat m-xylene. To determine whether acceptable yields for methyl-substituted arenes could be obtained, 1 equiv of HBPin was used for the borylation of m-xylene in cyclohexane. The aryl and benzyl boronate esters were separated, with the aryl product being favored by a factor of about 9:1. For 3-methylanisole, a modest excess of HBPin was used and the 1,3,5-substituted major product was readily obtained in 54% yield after chromatography. Entries 7 and 9 demonstrate that preference for borylation at the 5-position holds for unsymmetrically substituted arenes. We attempted the borylation of m-dichlorobenzene and found a mixture of products with unreacted arene, chlorobenzene, ClC$_6$H$_4$(BPin), and Cl$_2$C$_6$H$_4$(BPin) isomers as the major species. This is not surprising since we previously observed competitive C—H and C—F activation using the same precatalyst for borylations of fluorinated arenas (Cho et al., J. Am. Chem. Soc. 2000, 122, 12868–12869. Consequently, no other halogenated arenes were examined. An attempted borylation of benzonitrile led to nitrile reduction instead of aromatic C—H activation.

Entries 10 and 11 represent extensions of directed borylations to 1,2-substituted arenes and pyrrole. For veratrole, two isomers were detected by GC in a 99:1 ratio with the expected major product being 1,2,4-C$_6$H$_3$(OMe)$_2$(BPin). After chromatographic purification, the major isomer was isolated in 82% yield. Direct borylations of pyrrole and trimethylsilyl pyrrole were ineffective. However, selective borylation at the less hindered 3-position could be achieved by increasing the steric bulk of the silyl protecting group. The regiochemistry of the borylation was verified by preparing the known phenyl-substituted pyrrole (Alvarez et al. J. Org. Chem. 1992, 57, 1653–1656) via the Suzuki coupling of the pyrrolyl boronate ester with $IC_6H_5$.

The pyrrole result represents an important extension of the arene chemistry because selective functionalization at the 3-position is considerably more difficult than at the 2-position. For example, the best reported synthesis of $3\text{-}^iPr_3SiNC_4H_3(B(OH)_2)$ involves iodination of $^iPr_3SiNC_4H_4$ by N-iodosuccinamide to afford $3\text{-}^iPr_3SiNC_4H_3I$, generation of the lithiated pyrrole with tBuLi, quenching with $B(OMe)_3$, and hydrolytic workup to afford the boronic acid in 27% yield from $^iPr_3SiNC_4H_4$ (Alvarez et al. J. Org. Chem. 1992, 57, 1653–1656). In a single step, the reaction in entry 11 of Table 3 provides a stable source of the boronic acid in 81% yield.

In summary, we have shown that cyclohexane can serve as an inert solvent for Rh-catalyzed borylations of arenes. In addition, selective borylation at the 5-position of 1,3-substituted arenes has been demonstrated for a broader range of substrates, including dimethyl resorcinol and 1,3-$(NMe_2)_2 C_6H_4$ where functionalizations at the 5-position are difficult. An example of regioselective borylation of a symmetric, 1,2-substituted arene has been demonstrated for veratrole. Last, $^iPr_3SiNC_4H_4$ has been selectively borylated at the less hindered 3-position in high yield.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A catalytic composition comprising:

an iridium complex of the formula: $(BY)_n$—Ir-(ligand)$_m$ with three or more n and m substituents, excluding hydrogen, bonded to the iridium BY is a boron moiety and the ligand is selected from the group consisting of a phosphorus organic ligand, an organic amine, an imine, a nitrogen heterocycle, and an ether wherein the ligand is at least in part bonded to the iridium.

2. The catalytic composition of claim 1 wherein the phosphorus organic ligand is selected from the group consisting of trimethyl phosphine (PMe$_3$), 1,2-bis(dimethylphosphino)ethane (dmpe), and 1,2-bis(diphenylphosphino)ethane (dppe).

3. The catalytic composition of claim 1 wherein the iridium complex is (ArH)Ir(BY)$_3$ wherein ArH is selected from the group consisting of aromatic, heteroaromatic, polyaromatic, and heteropolyaromatic hydrocarbon; and BY is a boron moiety of the formula

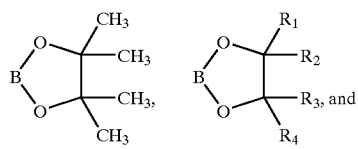

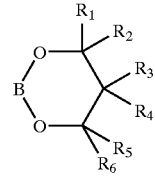

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure.

4. The catalytic composition of claim 1 wherein the iridium complex is (MesH)Ir(BY)$_3$ wherein MesH is mesitylene; and BY is a boron moiety selected from the group consisting of

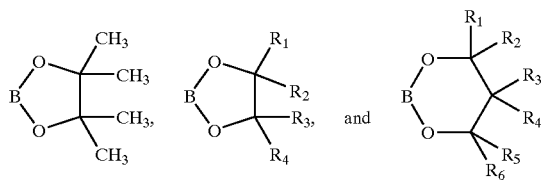

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure.

5. The catalytic composition of claim 1 wherein the iridium complex is $(P(Y_4)(Y_5)(Y_6))_3Ir\ (H)_n(BY)_{3-n}$ wherein $Y_4$, $Y_5$, and $Y_6$ are each selected from the group consisting of hydrogen, halide, alkyl, aryl, alkoxide (—O(R$_{11}$)), and amide (—N(R$_{12}$)(R$_{13}$)) wherein R$_{11}$, R$_{12}$, and R$_{13}$ are each selected from the group consisting of hydrogen, linear alkyl containing 1 to 8 carbon atoms, branched alkyl containing 1 to 8 carbons, and a carbon in a cyclic structure; n is 0, 1, or 2; and BY is a boron moiety selected from the group consisting of

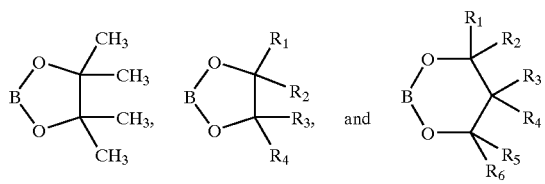

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure.

6. The catalytic composition of claim 1 wherein the iridium complex is $(P(R_{14})(R_{15})(R_{16}))_3Ir\ (H)_n(BY)_{3-n}$ wherein R$_{11}$, R$_{12}$, and R$_{13}$ are each selected from the group consisting of hydrogen, linear alkyl, branched alkyl, and a carbon in a cyclic structure; n is 0, 1, or 2; and BY is a boron moiety selected from the group consisting of

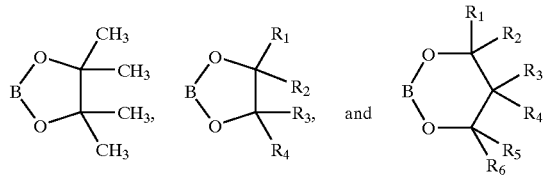

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure.

7. The catalytic composition of claim 1 wherein the iridium complex is $(P(Y_4)(Y_5)(Y_6))_3Ir\ (H)(R_{17})(BY)$ wherein $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; $R_{17}$ is selected from the group consisting of a linear alkyl containing 1 to 8 carbon atoms, branched alkyl containing 1 to 8 carbons, aryl, and a carbon in a cyclic structure; and BY is a boron moiety selected from the group consisting of

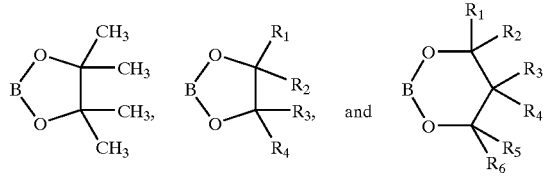

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure.

8. The catalytic composition of claim 1 wherein the iridium complex is $(P(R_{14})(R_{15})(R_{16}))_3Ir\ (H)(R_{17})(BY)$ wherein $R_{14}$, $R_{15}$, and $R_{16}$ are each selected from the group consisting of hydrogen, linear alkyl, branched alkyl, and a carbon in a cyclic structure; $R_{17}$ is selected from the group consisting of a linear alkyl containing 1 to 8 carbon atoms, branched alkyl containing 1 to 8 carbons, aryl, and a carbon in a cyclic structure; and BY is a boron moiety selected from the group consisting of

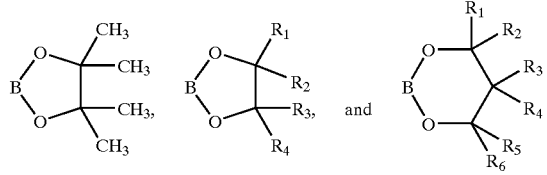

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure.

9. The catalytic composition of claim 1 wherein the iridium complex is $\{(PY_7P)Ir(BY)_3\}_2(\mu_2\text{-}(PY_7P))$ wherein BY is a boron moiety selected from the group consisting of

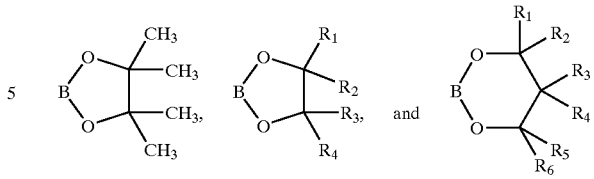

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; $(PY_7P)$ is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

10. The catalytic composition of claim 1 wherein the iridium complex is $(PY_7P)(P(Y_4)(Y_5)(Y_6))Ir(BY)_3$ wherein BY is a boron moiety selected from the group consisting of

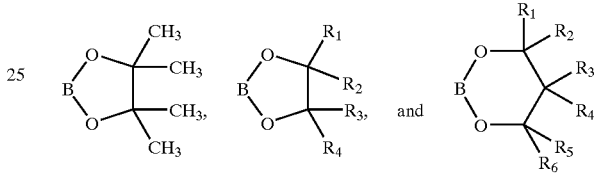

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; $Y_4$, $Y_5$, and $Y_6$ are each selected from the group consisting of hydrogen, halide, alkyl, aryl, alkoxide (—O($R_{11}$)), and amide (—N($R_{12}$)($R_{13}$)) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and $(PY_7P)$ is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

11. The catalytic composition of claim 1 wherein the iridium complex is $(PY_7P)(P(R_{14})(R_{15})(R_{16}))Ir(BY)_3$ wherein BY is a boron moiety selected from the group consisting of

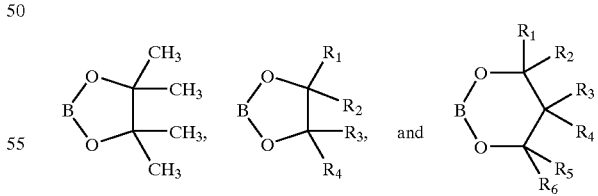

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; $R_{14}$, $R_{15}$, and $R_{16}$ are each selected from the group consisting of hydrogen, linear alkyl, branched alkyl, and a carbon in a cyclic structure; $(PY_7P)$ is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

12. The catalytic composition of claim 1 wherein the iridium complex is $\{(P^\frown P)Ir(BY)_3\}_2(\mu_2\text{-}(P^\frown P))$ wherein BY is a boron moiety selected from the group consisting of

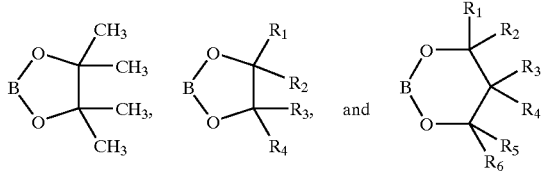

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; and wherein $(P^\frown P)$ is of the formula

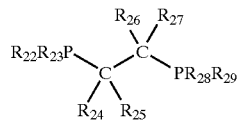

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

13. The catalytic composition of claim 1 wherein the iridium complex is $(P^\frown P)(P(Y_4)(Y_5)(Y_6))Ir(BY)_3$ wherein BY is a boron moiety selected from the group consisting of

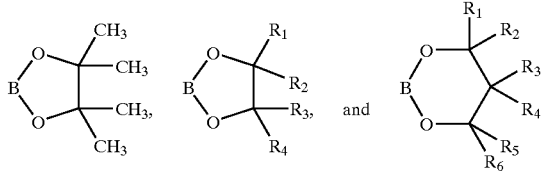

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; $Y_4$, $Y_5$, and $Y_6$ are each selected from the group consisting of hydrogen, halide, alkyl, aryl, alkoxide ($-O(R_{11})$), and amide ($-N(R_{12})(R_{13})$) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and wherein $(P^\frown P)$ is of the formula

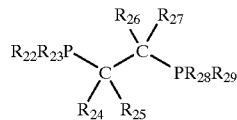

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

14. The catalytic composition of claim 1 wherein the iridium complex is $(P^\frown P)(P(R_{14})(R_{15})(R_{16}))Ir(BY)_3$ wherein BY is a boron moiety selected from the group consisting of

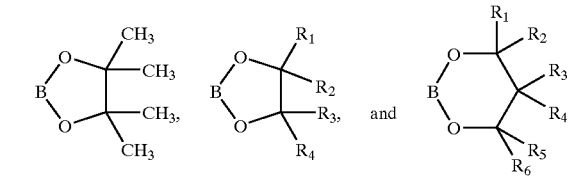

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; $R_{14}$, $R_{15}$, and $R_{16}$ are each selected from the group consisting of hydrogen, linear alkyl, branched alkyl, and a carbon in a cyclic structure; and wherein $(P^\frown P)$ is of the formula

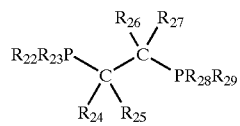

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

15. The catalytic composition of claim 1 wherein the iridium complex is $(PY_7P)Ir(BY)_3$ wherein BY is a boron moiety selected from the group consisting of

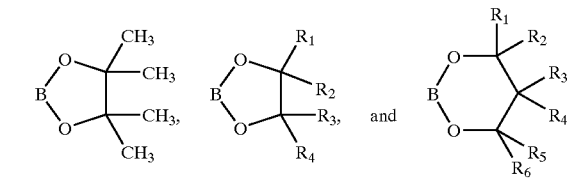

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; and $(PY_7P)$ is $R_{18}R_{19}P-Y_7-PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

16. The catalytic composition of claim 1 wherein the iridium complex is $(P^\frown P)Ir(BY)_3$ wherein BY is a boron moiety selected from the group consisting of

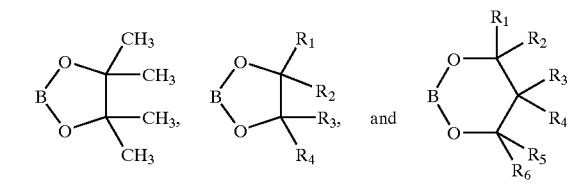

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; and wherein $(P^\frown P)$ is of the formula

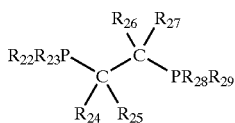

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

17. The catalytic composition of claim 1 wherein the iridium complex is $(P(Y_4)(Y_5)(Y_6))_4Ir(BY)$ wherein $Y_4$, $Y_5$, and $Y_6$ are each selected from the group consisting of hydrogen, halide, alkyl, aryl, alkoxide ($—O(R_{11})$), and amide ($—N(R_{12})(R_{13})$) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and BY is a boron moiety selected from the group consisting of

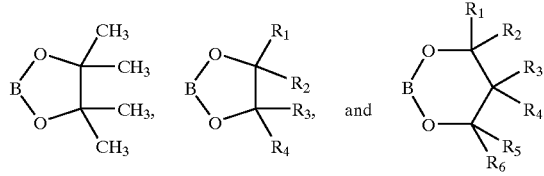

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure.

18. The catalytic composition of claim 1 wherein the iridium complex is $(P(R_{14})(R_{15})(R_{16}))_4Ir(BY)$ wherein $R_{14}$, $R_{15}$, and $R_{16}$ are each selected from the group consisting of hydrogen, linear alkyl, branched alkyl, and a carbon in a cyclic structure; and BY is a boron moiety selected from the group consisting of

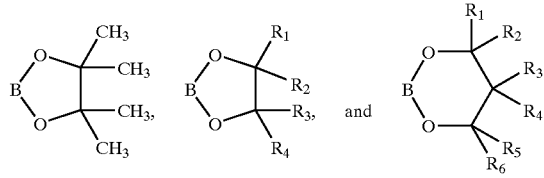

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure.

19. The catalytic composition of claim 1 wherein the iridium complex is $(PY_7P)(P(Y_4)(Y_5)(Y_6))_2Ir(BY)$ wherein BY is a boron moiety selected from the group consisting of

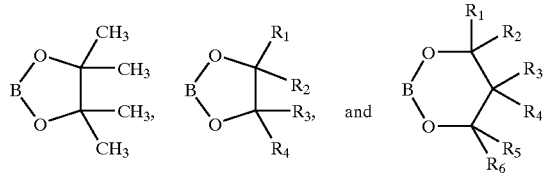

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; $Y_4$, $Y_5$, and $Y_6$ are each selected from the group consisting of hydrogen, halide, alkyl, aryl, alkoxide ($—O(R_{11})$), and amide ($—N(R_{12})(R_{13})$) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and $(PY_7P)$ is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

20. The catalytic composition of claim 1 wherein the iridium complex is $(P^{\frown}P)(P(Y_4)(Y_5)(Y_6))_2Ir(BY)$ wherein BY is a boron moiety selected from the group consisting of

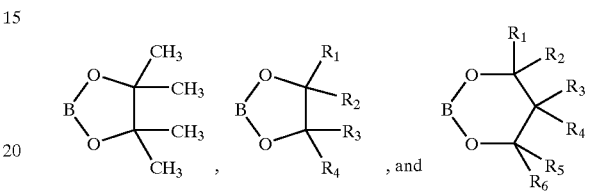

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; $Y_4$, $Y_5$, and $Y_6$ are each selected from the group consisting of hydrogen, halide, alkyl, aryl, alkoxide ($—O(R_{11})$), and amide ($—N(R_{12})(R_{13})$) wherein $R_{11}$, $R_{12}$, and $R_{13}$ are each selected from the group consisting of hydrogen, linear alkyl containing 1 to 8 carbon atoms, branched alkyl containing 1 to 8 carbons, and a carbon in a cyclic structure; and wherein $(P^{\frown}P)$ is of the formula

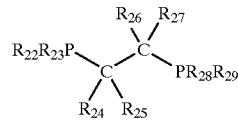

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

21. The catalytic composition of claim 1 wherein the iridium complex is $(PY_7P)(P(R_{14})(R_{15})(R_{16}))_2Ir(BY)$ wherein BY is a boron moiety selected from the group consisting of

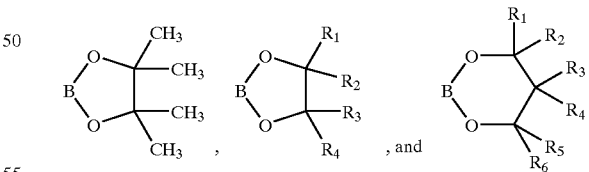

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; $R_{14}$, $R_{15}$, and $R_{16}$ are each selected from the group consisting of hydrogen, linear alkyl, branched alkyl, and a carbon in a cyclic structure; $(PY_7P)$ is $R_{18}R_{19}P—Y_7—PR_{20}R_{21}$ wherein $R_{18}$, $R_{19}$, $R_{20}$, and $R_{21}$ are each selected from the group consisting of hydrogen, linear alkyl containing 1 to 8 carbon atoms, branched alkyl containing 1 to 8 carbons, and a carbon in a cyclic structure, and $Y_7$ is a chain containing 1 to 12 carbons.

22. The catalytic composition of claim 1 wherein the iridium complex is $(P\frown P)(P(R_{14})(R_{15})(R_{16}))_2Ir(BY)$ wherein BY is a boron moiety selected from the group consisting of

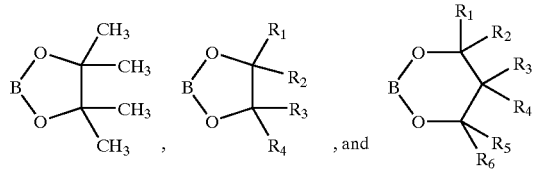

wherein $R_1$, $R_2$, $R_3$, $R_4$, $R_5$, and $R_6$ are each selected from the group consisting of hydrogen, linear alkyl containing 1 to 8 carbon atoms, branched alkyl containing 1 to 8 carbons, and a carbon in a cyclic structure; $R_{14}$, $R_{15}$, and $R_{16}$ are each selected from the group consisting of hydrogen, linear alkyl, branched alkyl, and a carbon in a cyclic structure; and wherein $(P\frown P)$ is of the formula

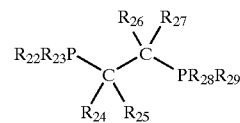

wherein $R_{22}$, $R_{23}$, $R_{24}$, $R_{25}$, $R_{26}$, $R_{27}$, $R_{28}$, and $R_{29}$ are each selected from the group consisting of alkyl chains, carbocyclic rings, and aryl groups.

23. The catalytic composition of claim 1 wherein the iridium complex is selected from the group consisting of $(Cp^*)Ir(H)_2(Me_3P)$, $(Cp^*)Ir(H)(BPin)(Me_3P)$, $(CP^*)Ir(H)(C_6H_5)(Me_3P)$, $(Ind)Ir(COD)$, $(MesH)Ir(BPin)(B(OR)_2)$, $((R_1)_3P)_3Ir(B(OR_2)_2)_3$, $(R_1)_2P)_2Ir(BPin)_3$, $[((R_1)_2P)_3Ir((R_2O)_2B)_3]_2$, $((R_1)_3P)_4Ir(BPin)$, $((R_1)_2P)_2Ir(BPin)_3$, $(MesH)Ir(BPin)_3$, $IrCl(COD)$, and $[IrCl(COD)]_2$, wherein CP* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and wherein R, $R_1$, and $R_2$ are each selected from the group consisting of hydrogen, linear or branched alkyl containing 1 to 8 carbons, aryl, and a carbon in a cyclic structure.

* * * * *

UNITED STATES PATENT AND TRADEMARK OFFICE
CERTIFICATE OF CORRECTION

PATENT NO.    : 6,878,830 B2
DATED         : April 12, 2005
INVENTOR(S)   : Milton R. Smith, III It is certified that error appears in the above-identified patent and that said Letters Patent is hereby corrected as shown below:

Column 17,
Line 64, "cross-couplingcheck reactions" should be -- cross-couplingreactions --.

Column 39,
Line 67, "and HBPin using" should be -- and HBPin using precatalyst 7 in cyclohexane. --.

Column 41,
Lines 41 and 48, "(NMez)(BPin)" should be -- (NMe2)(Bpin)--

Column 52,
Line 55, "fluorinatedarenas" should be -- fluorinated arenes --.

Signed and Sealed this

Nineteenth Day of July, 2005

JON W. DUDAS
*Director of the United States Patent and Trademark Office*

UNITED STATES PATENT AND TRADEMARK OFFICE
CERTIFICATE OF CORRECTION

PATENT NO. : 6,878,830 B2  
APPLICATION NO. : 10/194809  
DATED : April 12, 2005  
INVENTOR(S) : Milton R. Smith, III Page 1 of 1

It is certified that error appears in the above-identified patent and that said Letters Patent is hereby corrected as shown below:

In the Specification

In column 1, lines 13-17, please delete:

"This invention was supported in part by National Institutes of Health, National Institute of General Medical Sciences Grant No. R01 GM63188-01 and in part by National Science Foundation Grant No. CHE-9817230. The U.S. government has certain rights in this invention."

and insert:

-- This invention was made with government support under GM063188 awarded by the National Institutes of Health, and under CHE9817230 awarded by the National Science Foundation. The government has certain rights in the invention. --

Signed and Sealed this  
Eighth Day of July, 2014

Michelle K. Lee  
*Deputy Director of the United States Patent and Trademark Office*